US008481067B2

(12) United States Patent
Zhang et al.

(10) Patent No.: US 8,481,067 B2
(45) Date of Patent: Jul. 9, 2013

(54) METHODS FOR PROMOTING THE REVASCULARIZATION AND REENERVATION OF CNS LESIONS

(75) Inventors: Ning Zhang, Charleston, SC (US); Xuejun Wen, Mount Pleasant, SC (US)

(73) Assignee: Clemson University Research Foundation, Clemson, SC (US)

( * ) Notice: Subject to any disclaimer, the term of this patent is extended or adjusted under 35 U.S.C. 154(b) by 53 days.

(21) Appl. No.: 12/794,556

(22) Filed: Jun. 4, 2010

(65) Prior Publication Data

US 2011/0091550 A1    Apr. 21, 2011

Related U.S. Application Data

(60) Provisional application No. 61/184,163, filed on Jun. 4, 2009.

(51) Int. Cl.
| | | |
|---|---|---|
| *A61L 27/14* | (2006.01) | |
| *A61L 27/22* | (2006.01) | |
| *A61L 27/52* | (2006.01) | |
| *A61L 27/54* | (2006.01) | |
| *A61K 31/727* | (2006.01) | |

(52) U.S. Cl.
USPC .......... 424/423; 424/422; 424/486; 514/17.7; 514/18.2

(58) Field of Classification Search
None
See application file for complete search history.

(56) References Cited

U.S. PATENT DOCUMENTS

| | | |
|---|---|---|
| 7,828,539 B1 | 11/2010 | Beachley et al. |
| 7,914,819 B1 | 3/2011 | Wen et al. |
| 8,124,001 B1 | 2/2012 | Wen et al. |
| 2003/0198619 A1* | 10/2003 | Dong et al. ............. 424/85.7 |
| 2006/0257368 A1 | 11/2006 | Wen |
| 2007/0077270 A1 | 4/2007 | Wen |
| 2011/0038921 A1 | 2/2011 | Wen et al. |
| 2012/0100185 A1 | 4/2012 | Wen et al. |

FOREIGN PATENT DOCUMENTS

| | | | |
|---|---|---|---|
| WO | WO 02102429 | * | 12/2002 |
| WO | WO 03040235 | * | 5/2003 |
| WO | WO 2010/120757 A2 | | 10/2010 |

OTHER PUBLICATIONS

Hou et al., J Neuroscience Methods, 148:60-70, 2005.*
Shu et al., Biomaterials, 25:1339-1348, published online Oct. 14, 2003.*
Jain et al., Biomaterials, 27:497-504, published online Aug. 15, 2005.*
Hannila et al., Experimental Neurology, 209:321-332, 2008.*
Hattori et al., J Clin Neurosci., 15: 185-191, 2008.*
Allen, Shelley J. et al., "Clinical relevance of the neurotrophins and their receptors", *Clinical Science*, vol. 110, 2006, pp. 175-191.
Bellamkonda, Ravi et al., "Hydrogel-based three-dimensional matrix for neural cells", *Journal of Biomedical Materials Research*, vol. 29, 1995, pp. 663-671.
Cai, Shenshen et al., "Injectable glycosaminoglycan hydrogels for controlled release of human basic fibroblast growth factor", *Biomaterials*, vol. 26, 2005, pp. 6054-6067.
Carmeliet, Peter, "Angiogenesis in health and disease", *Nature Medicine*, vol. 9 No. 6, Jun. 2003, pp. 653-660.
Cho, Youngnam et al., "Chitosan produces potent neuroprotection and physiological recovery following traumatic spinal cord injury", *The Journal of Experimental Biology*, vol. 213, pp. 1513-1520.
Crompton K.E. et al., "Polylysine-functionalised thermoresponsive chitosan hydrogel for neural tissue engineering", *Biomaterials*, vol. 28, 2007, pp. 441-449.
Deguchi, Kentaro et al., "Implantation of a new porous gelatin-siloxane hybrid into a brain lesion as a potential scaffold for tissue regeneration", *Journal of Cerebral Blood Flow & Metabolism*, vol. 26, 2006, pp. 1263-1273.
Eagle, K.S. et al., "Axonal Regeneration and Limited Functional Recovery Following Hippocampal Deafferentation", *The Journal of Comparative Neurology*, vol. 363, 1995, pp. 377-388.
Freier, Thomas et al., "Controlling cell adhesion and degradation of chitosan films by N-acetylation", *Biomaterials*, vol. 26, 2005, pp. 5872-5878.
Gamez, Eduardo et al., "Photofabricated Gelatin-Based Nerve Conduits: Nerve Tissue Regeneration Potentials", *Cell Transplantation*, vol. 13, 2004, pp. 549-564.
Gupta, Dimpy et al., "Fast-gelling injectable blend of hyaluronan and methylcellulose for intrathecal, localized delivery to the injured spinal cord", *Biomaterials*, vol. 27, 2006, pp. 2370-2379.
Horn, Eric M. et al., "Influence of cross-linked hyaluronic acid hydrogels on neurite outgrowth and recovery from spinal cord injury", *J. Neurosurg Spine*, vol. 6, 2007, pp. 133-140.
Hou, Shaoping et al. "The repair of brain lesion by implantation of hyaluronic acid hydrogels modified with laminin", *Journal of Neuroscience Methods*, vol. 148, 2005, pp. 60-70.
Imitola, Jaime et al., "Directed migration of neural stem cells to sites of CNS injury by the stromal cell-derived factor 1α/CXC chemokine receptor 4 pathway", *PNAS*, Dec. 28, 2004, vol. 101, No. 52, pp. 18117-18122.
Klaver, Christopher L. et al., "Bioactive surface for neural electrodes: Decreasing astrocyte proliferation via transforming growth factor-β1", *J Biomed Mater Res 81A*, 2007, pp. 1011-1016.

(Continued)

*Primary Examiner* — Daniel E Kolker
*Assistant Examiner* — Stacey N MacFarlane
(74) *Attorney, Agent, or Firm* — Myers Bigel Sibley & Sajovec, P.A.

(57) ABSTRACT

The present invention provides methods of promoting the revascularization and/or reenervation of central nervous system lesions using an in-situ crosslinkable hydrogel.

16 Claims, 13 Drawing Sheets

OTHER PUBLICATIONS

Laurent, Torvard C. et al., "The structure and function of hyaluronan: An overview" *Immunol Cell Biol*, Apr. 1996, 74 (2), A1-7.

Leach, Jennie B. et al., "Development of photocrosslinkable hyaluronic acid-polyethylene glycol-peptide composite hydrogels for soft tissue engineering", *J Biomed Mater Res*, vol. 70A, 2004, pp. 74-82.

Lu, Dunyue et al., "Collagen scaffolds populated with human marrow stromal cells reduce lesion volume and improve functional outcome after traumatic brain injury", *Neurosurgery*, vol. 61, No. 3, Sep. 2007, pp. 596-603.

Luo, Yi et al., "Cross-linked hyaluronic acid hydrogel films: new biomaterials for drug delivery", *Journal of Controlled Release*, vol. 69, 2000, pp. 169-184.

Murphy, Joseph F. et al., "Engagement of CD44 modulates cyclooxygenase induction, VEGF generation, and proliferation in human vascular endothelial cells", *The FASEB Journal*, vol. 19, Mar. 2005, pp. 446-448.

Nicholas Florence L. et al. "Denatured Thiolated Collagen" *Biomaterials*, vol. 18, 1997, pp. 807-813.

Peattie, R. A. et al., "Stimulation of in vivo angiogenesis by cytokine-loaded hyaluronic acid hydrogel implants", *Biomaterials*, vol. 25, 2004, pp. 2789-2798.

Peattie, Robert A. et al., "Dual growth factor-induced angiogenesis in vivo using hyaluronan hydrogel implants" *Biomaterials*, vol. 27, 2006, pp. 1868-1875.

Plant, GW et al. "Implantation of Collagen IV/poly(2-hydroxyethyl Methacrylate) Hydrogels Containing Schwann Cells into the Lesioned Rat Optic Tract" *Cell Transplant*, vol. 4, 1998, pp. 381-391.

Prestwich, Glenn D. et al., "Injectable synthetic extracellular matrices for tissue engineering and repair", *Adv Exp Med Biol*, vol. 585, 2007, pp. 125-133.

Qiu, Yongzhi et al., "Chemically modified light-curable chitosans with enhanced potential for bone tissue repair", *J Biomed Mater Res 89A*, 2009, pp. 772-779.

Qiu, Yongzhi et al., "Fabrication of Permeable Tubular Constructs From Chemically Modified Chitosan With Enhanced Antithrombogenic Property", *J Biomed Mater Res Part B: Appl Biomater 90B*, 2009, pp. 668-678.

Radice M. et al., "Hyaluronan-based biopolymers as delivery vehicles for bone-marrow-derived mesenchymal progenitors", *J Biomed Mater Res*, vol. 50, 2000, pp. 101-109.

Reichardt, Louis F., "Neurotrophin-regulated signalling pathways", *Phil. Trans. R. Soc. B*, 2006, vol. 361, pp. 1545-1564.

Riley, Celeste M. et al., "Stimulation of in vivo angiogenesis using dual growth factor-loaded crosslinked glycosaminoglycan hydrogels", *Biomaterials*, 27 (35), 2006, pp. 5935-5943.

Sanes, Joshua R., "Roles of Extracellular Matrix in Neural Development", *Ann. Rev. Physiol.* 1983, vol. 45, pp. 581-600.

Segura, Tatiana et al., "Crosslinked hyaluronic acid hydrogels: a strategy to functionalize and pattern", *Biomaterials*, vol. 26, 2005, pp. 359-371.

Shu, Xiao Zheng et al., "Attachment and spreading of fibroblasts on an RGD peptide-modified injectable hyaluronan hydrogel", *J Biomed Mater Res*, vol. 68A, 2004, pp. 365-375.

Shu, Xiao Zheng et al., "Disulfide Cross-Linked Hyaluronan Hydrogels", *Biomacromolecules*, vol. 3, 2002, pp. 1304-1311.

Shu, Xiao Zheng et al., "Disulfide-crosslinked hyaluronan-gelatin hydrogel films: a covalent mimic of the extracellular matrix for in vitro cell growth", *Biomaterials*, vol. 24, 2003, 3825-3834.

Shu, Xiao Zheng et al., "In situ crosslinkable hyaluronan hydrogels for tissue engineering", *Biomaterials*, vol. 25, 2004, pp. 1339-1348.

Shu, Xiao Zheng et al., "Synthesis and evaluation of injectable, in situ crosslinkable synthetic extracellular matrices for tissue engineering", *J Biomed Mater Res*, vol. 79A, 2006, pp. 902-912.

Solchaga, Luis A. et al., "Hyaluronan-based Polymers in the Treatment of Osteochondral Defects", *Journal of Orthopaedic Research*, vol. 18, No. 5, 2000, pp. 773-780.

Stabenfeldt, Sarah E. et al., "Thermoreversible laminin-functionalized hydrogel for neural tissue engineering", *J Biomed Mater Res 77A*, 2006, pp. 718-725.

Tate, Matthew C. et al., "Biocompatibility of methylcellulose-based constructs designed for intracerebral gelation following experimental traumatic brain injury", *Biomaterials*, vol. 22, 2001, pp. 1113-1123.

Tian, W.M. et al., "Hyaluronic Acid-Poly-D-Lysine-Based Three-Dimensional Hydrogel for Traumatic Brain Injury", *Tissue Engineering*, vol. 11, No. 3/4, 2005, pp. 513-528.

Trochon, Veronique et al., "Evidence of Involvement of CD44 in Endothelial Cell Proliferation, Migration and Angiogenesis In Vitro", *Int. J. Cancer*, vol. 66, 1996, pp. 664-668.

Wade, Charles et al., "Efficacy of hypertonic saline dextran (HSD) in patients with traumatic hypotension: meta-analysis of individual patient data", *Acta Anaesthesiol Scand Suppl*, vol. 110, 1997, pp. 77-79.

Wei, Y.T. et al., "Hyaluronic acid hydrogels with IKVAV peptides for tissue repair and axonal regeneration in an injured rat brain", *Biomed. Mater.* vol. 2, 2007, pp. S142-S146.

Wells, Michael R. et al., "Gel Matrix Vehicles for Growth Factor Application in Nerve Gap Injuries Repaired with Tubes: A Comparison of Biomatrix, Collagen, and Methylcellulose", *Experimental Neurology*, vol. 146, 1997, pp. 395-402.

Wissink, M.J.B. et al., "Binding and release of basic fibroblast growth factor from heparinized collagen matrices", *Biomaterials*, vol. 22, 2001, pp. 2291-2299.

Wissink, M.J.B. et al., "Immobilization of heparin to EDC/NHS-crosslinked collagen. Characterization and in vitro evaluation", *Biomaterials*, vol. 22, 2001, pp. 151-163.

Woerly S. et al., "Neural Tissue Formation Within Porous Hydrogels Implanted in Brain and Spinal Cord Lesions: Ultrastructural, Immunohistochemical, and Diffusion Studies", *Tissue Eng*, vol. 5, No. 5, 1999, pp. 467-488.

Zhang, Changhong et al., "Synthesis and characterization of biocompatible, degradable, light-curable, polyurethane-based elastic hydrogels", *J Biomed Mater Res 82A*, 2007, pp. 637-650.

Zhang, Ning et al., "Fabrication of semipermeable hollow fiber membranes with highly aligned texture for nerve guidance", *J Biomed Mater Res 75A*, 2005, pp. 941-949.

Zhang, Ning, et al., "Tissue-engineering approaches for axonal guidance", *Brain Research Reviews*, vol. 49, 2005, pp. 48-64 (abstract).

Zhang Ning, et al. "Drug-Loaded Degradable Nano-Particles for the Rescue of Tissue Under Hypoxia Condition and Promote Angiogenesis" 229th ACS National Meeting, San Diego, CA Mar. 13, 2005.

Zhao, Jing et al., "Recruitment of Endogenous Stem Cells for Tissue Repair", *Macromol. Biosci.*, vol. 8, 2008, pp. 836-842.

Zhong, Yinghui et al., "Controlled release of anti-inflammatory agent α-MSH from neural implants", *Journal of Controlled Release*, vol. 106, 2005, pp. 309-318.

* cited by examiner

SEQUENCE LISTING

```
<160> NUMBER OF SEQ ID NOS: 1

<210> SEQ ID NO 1
<211> LENGTH: 25
<212> TYPE: PRT
<213> ORGANISM: Artificial
<220> FEATURE:
<223> OTHER INFORMATION: Laminin-derived short peptide sequence

<400> SEQUENCE: 1

Cys Asp Pro Val Cys Cys Gly Thr Ala Arg Pro Gly Tyr Ile Gly Ser
1               5                   10                  15

Arg Gly Thr Ala Arg Cys Cys Ala Cys
            20                  25
```

METHODS FOR PROMOTING THE REVASCULARIZATION AND REENERVATION OF CNS LESIONS

PRIORITY STATEMENT

This application claims the benefit, under 35 U.S.C. §119 (e), of U.S. Provisional Application Ser. No. 61/184,163, filed Jun. 4, 2009, the entire contents of which are incorporated by reference herein.

STATEMENT REGARDING ELECTRONIC FILING OF A SEQUENCE LISTING

A Sequence Listing in ASCII text format, submitted under 37 C.F.R. §1.821, entitled 9662-4 ST25.txt, 672 bytes in size, generated on Jun. 22, 2012 and filed via EFS-Web, is provided in lieu of a paper copy. This Sequence Listing is incorporated herein by reference into the specification for its disclosures.

FIELD OF THE INVENTION

The present invention relates to methods of promoting the revascularization and/or reenervation of central nervous system lesions.

BACKGROUND OF THE INVENTION

Brain stroke ranks as the third leading cause of death and disability in most developed countries (Wolfe et al., *J. Neurol. Neurosurg. Psychiatry* 72:211 (2002), and is the second most common cause of death worldwide (Murray et al., *Lancet* 349:1269 (1997)). About ⅙ of all human beings will suffer at least one stroke in their lives (Seshadri et al., *Stroke* 37:345 (2006)). Stroke can be hemorrhagic, ischemic, or embolic in origin. Each year, 500,000 new cases of brain strokes are reported in the US (Higashida et al., *Am. J. Neuroradiol.* 26:2323 (2005)). Depending upon the particular cerebral vessels involved, stroke patients may have a one-year mortality rate ranging from 60% to 8% (Murray et al., *Lancet* 349:1269 (1997); Salgado et al., *Stroke* 27:661 (1996)). Nonetheless, the surviving stroke patients usually remain severely disabled and require constant care for the rest of their lives.

Despite tremendous effort in thrombolysis and neuroprotection, no effective treatment is available for cerebral stroke in clinical settings. This is largely due to the inability of current treatments to repopulate the stroke lesion cavity with functional neurons and glial cells, which dynamically participate in cell-cell signaling and provide sustained trophic support that is critical for decreased neural degeneration and sustained functional recovery. In support of this notion, neural transplantation strategies have been developed to reconstruct the stroke lesion cavity. Despite its efficacy in providing sustained functional recovery in other types of central nervous system (CNS) injuries, neural transplantation for cerebral stroke repair has had limited success, due to poor donor cell survival and functionality at the infarct site (Savitz et al., *NeuroRx* 1:406 (2004)).

An accumulating body of evidence has indicated the predominant role of glial scar tissue in obstructing brain tissue regeneration and structural repair following stroke (Lipton, *Physiol. Rev.* 79:1431 (1999); Gartshore et al., *Exp. Neurol.* 147:353 (1997)). The dense scar tissue outlining a stroke lesion cavity typically consists of endogenous and/or hematogenous inflammatory cells embedded within a dense, remodeling extracellular matrix (Fitch et al., *J. Neurosci.* 19:8182 (1999); Lindsay, Reactive gliosis. In: Fedoroff S, Vernadakis A, editors. *Astrocytes* Orlando: Academic Press; 1986. pp. 231-262; Preston et al., *J. Neurotrauma* 18:83 (2001)). The presence of the scar tissue not only contributes to regenerative failure, but also to the poor survival and functionality of transplanted cells, and poses a diffusive barrier that hinders the effective delivery of nutrients, oxygen, and pharmacological agents into the lesion cavity.

Since any reparative therapy designed to regenerate brain tissue following a stroke will take place in the lesion site, there is a critical need for strategies to overcome the inhibitory scar and promote neuronal regeneration and reconstruction across the lesion cavity. Most importantly, a well-structured vasculature network that completely re-fills the stroke lesion cavity is a prerequisite to support the brain tissue regeneration process.

The present invention overcomes these shortcomings by providing methods for promoting revascularization and/or reenervation of CNS lesions. The methods may be accompanied by removal of existing scar tissue and/or prevention of scar tissue formation.

SUMMARY OF THE INVENTION

A first aspect of the present invention relates to methods of promoting revascularization in a CNS lesion, comprising delivering to the lesion an amount of a hydrogel of this invention effective to promote revascularization of the lesion. In one embodiment, the hydrogel does not comprise any angiogenic factors.

A further aspect of the present invention relates to methods of promoting revascularization and reenervation of a CNS lesion and/or repair/regeneration of a CNS lesion, comprising delivering to the lesion an amount of a hydrogel of this invention effective to promote revascularization and reenervation of the lesion.

A further aspect of the present invention relates to methods of recruiting neural stem cells to a CNS lesion, comprising delivering a hydrogel of this invention that contains at least one neural stem cell recruiting factor to the lesion in an amount effective to promote both revascularization of the lesion and recruitment of neural stem cells to the lesion. In certain embodiments, the neural stem cell recruiting factor is selected from the group consisting of hepatocyte growth factor, gliotropic factors (e.g., human recombinant annexin A2), stem cell factor-1, stromal cell-derived factor-1 (SDF-1), chemokine monocyte chemoattractant protein-1 (MCP-1, SCYA2, CCL2, MCAF), vascular endothelial growth factor (VEGF), epidermal growth factor (EGF), transmembrane protein 18, glioma-produced ECM (tenascin-C), IGF-1, FGF-2, PDGF and any combination thereof in any ratio.

A further aspect of the present invention relates to methods of repopulating a CNS lesion with functional neurons, comprising delivering a hydrogel of this invention that contains at least one neural stem cell recruiting factor and neurogenic factor to the lesion in an amount effective to promote both revascularization of the lesion and repopulation of the lesion with functional neurons. In certain embodiments, the neural stem cell recruiting factor is selected from the group consisting of hepatocyte growth factor, gliotropic factors (e.g., human recombinant annexin A2), stem cell factor-1, stromal cell-derived factor-1 (SDF-1), chemokine monocyte chemoattractant protein-1 (MCP-1, SCYA2, CCL2, MCAF), vascular endothelial growth factor (VEGF), epidermal growth factor (EGF), transmembrane protein 18, glioma-produced ECM (tenascin-C), IGF-1, FGF-2, PDGF and any combination thereof in any ratio.

A further aspect of the present invention relates to methods of repopulating a CNS lesion with functional neurons, comprising delivering a hydrogel of this invention that contains at least one mitogen for neural stem cell proliferation/expansion to the lesion in an amount effective to promote both revascularization of the lesion and repopulation of the lesion with functional neurons. In some embodiments, the mitogen for neural stem cells is selected from the group consisting of EGF, FGF-2, PDGF in any combination thereof in any ratio.

A further aspect of the present invention relates to methods of repopulating a CNS lesion with functional neurons, comprising delivering a hydrogel of this invention that contains at least one neural differentiation factor to the lesion in an amount effective to promote both revascularization of the lesion and repopulation of the lesion with functional neurons. In certain embodiments, the neural differentiation factor is selected from the group consisting of BDNF, NT-3, GDNF, CNTF and any combination thereof in any ratio.

A further aspect of the present invention relates to methods of repopulating a CNS lesion with functional neurons, comprising delivering a hydrogel of this invention to the lesion in an amount effective to promote revascularization of the lesion, and delivering at least one neural stem cell mobilizing factor to the central nervous system (CNS) of the subject having the lesion. In certain embodiments, the neural stem cell mobilizing factor is delivered to the subventricular zone. In some embodiments, the neural stem cell mobilizing factor is selected from the group consisting of leukemia inhibitory factor, granulocyte-colony stimulating factor and any combination thereof in any ratio.

An further aspect of the present invention relates to methods of repopulating a CNS lesion with functional neurons, comprising: delivering a hydrogel of this invention to the lesion in an amount effective to promote revascularization of the lesion, and delivering both a neural stem cell recruiting factor and a neural stem cell mobilizing factor to the CNS of the subject having the lesion. In certain embodiments, the neural stem cell recruiting factor is present in the hydrogel and the neural stem cell mobilizing factor is delivered to the subventricular zone. In other embodiments, the neural stem cell recruiting factor is hepatocyte growth factor and the neural stem cell mobilizing factor is leukemia inhibitory factor.

A further aspect of the present invention relates to methods of repairing a CNS lesion, comprising delivering to the lesion an amount of a hydrogel of this invention effective to promote the revascularization and reenervation of the lesion, thereby repairing the CNS lesion.

A further aspect of the present invention relates to methods of treating a disorder resulting from a CNS lesion, comprising delivering to the lesion an amount of a hydrogel of this invention effective to promote the revascularization and reenervation of the lesion and to treat at least one symptom of the disorder resulting from the CNS lesion.

A further aspect of the present invention relates to methods of preventing scar tissue growth in a CNS lesion, comprising delivering to the lesion an amount of a hydrogel of this invention comprising at least one agent that blocks the biosynthesis of inhibitory ECM components, wherein said amount is effective to prevent scarring. In certain embodiments, the agent is selected from the group consisting of p-nitrophenyl-b-D-xylopyranoside, dimethyloxalylglycine, cyclic nucleotides, and any combinations thereof in any ratio.

A further aspect of the present invention relates to methods of digesting scar tissue in a CNS lesion, comprising delivering to the lesion an amount of a hydrogel of this invention comprising at least one ECM-degrading enzyme, wherein said amount is effective to digest scar tissue. In certain embodiments, the enzyme is selected from the group consisting of chondroitinase ABC, collagenase IV, and any combination thereof in any ratio.

A further aspect of the present invention relates to methods of maintaining a scar-reduced environment in a CNS lesion, comprising delivering to the lesion an amount of a hydrogel of this invention comprising at least one agent that blocks the biosynthesis of inhibitory ECM components and, optionally, at least one ECM-degrading enzyme, wherein said amount is effective to maintain a scar-reduced environment. In certain embodiments, the agent is selected from the group consisting of p-nitrophenyl-b-D-xylopyranoside, dimethyloxalylglycine, cyclic nucleotides, and any combination thereof, and the enzyme is selected from the group consisting of chondroitinase ABC, collagenase IV, and any combination thereof.

In the methods of this invention, a pure synthetic hydrogel, a extracellular matrix (ECM) based hydrogel, a chemically modified ECM based hydrogel, or a mixture of synthetic and ECM based hydrogels can be used.

In some embodiments of the foregoing, the ECM-based hydrogel comprises at least one ECM molecule. In other embodiments, the hydrogel comprises at least two different ECM molecules. Said ECM molecule(s) may be chemically modified, such as by the addition of a thiol group. In some embodiments, the hydrogel may comprise hyaluronic acid, collagen, heparin, laminin, gelatin, fibronectin, and/or chitosan. In certain embodiments, the hydrogel comprises both hyaluronic acid and collagen. In other embodiments, the ratio of hyaluronic acid to collagen ranges from about 10:1 to about 1:10, e.g., about 1:3. Further embodiments may comprise hyaluronic acid, collagen, and laminin. In certain embodiments, the hydrogel comprises both hyaluronic acid and gelatin. In other embodiments, the ratio of hyaluronic acid to gelatin ranges from about 10:1 to about 1:10, e.g., about 1:3. Further embodiments may comprise hyaluronic acid, gelatin, and laminin. Poly(ethylene glycol) tetra-acrylate (PEGTA) or PEGDA can be used as crosslinker for gelation. The concentration of PEGTA or PEGDA can be from about 0.01% to about 20%.

In some embodiments of the foregoing, the hydrogel comprises at least one synthetic molecule. In other embodiments, the hydrogel comprises at least two (e.g., 3, 4, 5, 6, 7, 8, 9, 10, etc.) different synthetic molecules. The synthetic molecule(s) may be chemically modified, such as by the addition of one or more thiol groups or acrylate groups. In some embodiments, the hydrogel may comprise polyethylene glycol (PEG), also known as polyethylene oxide (PEO), synthetic peptide sequences (e.g., laminin like short peptide sequences, fibronectin like peptide sequences, collagen like peptide sequences, etc.). In certain embodiments, the hydrogel comprises both thiolated PEG and thiolated laminin short peptide sequences. In other embodiments, the ratio of thiolated PEG to thiolated peptide sequence ranges from about 10:1 to about 1:10, e.g., about 1:3. Further embodiments may comprise thiolated PEG, thiolated peptide sequence from fibronectin, etc. PEG can be single arm to multi-arm (e.g., 1, 2, 3, 4, 5, 6, 7, 8, 9, or 10 arms). Poly(ethylene glycol) tetra-acrylate (PEGTA) or PEGDA can be used as crosslinker for gelation. The concentration of PEGTA or PEGDA can be from about 0.01% to about 20%.

In some embodiments of the foregoing, the hydrogel comprises at least one synthetic molecule and one ECM. In other embodiments, the hydrogel comprises two or more (e.g., 2, 3, 4, 5, 6, 7, 8, 9, 10, etc.) different synthetic molecules and two or more (e.g., 2, 3, 4, 5, 6, 7, 8, 9, 10, etc.) ECMs. The synthetic molecule(s) or ECM(s) may be chemically modified, such as by the addition of one or more thiol groups or acrylate groups. In some embodiments, the hydrogel may comprise polyethylene glycol, synthetic peptide sequences, hyaluronic acid, and gelatin. In certain embodiments, the hydrogel comprises both thiolated PEG, thiolated laminin short peptide sequences, thiolated hyaluronic acid, and thiolated gelatin. In other embodiments, the ratio of thiolated PEG:thiolated peptide sequence:thiolated hyaluronic acid: thiolated gelatin ranges from about 10:1:1:1 to about 1:1:1: 10, e.g., about 4:3:2:1. Further embodiments may comprise thiolated PEG, thiolated peptide sequence from fibronectin, etc. PEG can be single arm to multi-arm (e.g., 1-10 arms). Poly(ethylene glycol) tetra-acrylate (PEGTA) or PEGDA can be used as crosslinker for gelation. The concentration of PEGTA or PEGDA can be from about 0.01% to about 20%.

In some embodiments of the present invention, the factor, agent, and/or enzyme present in the hydrogel is loaded into nanoparticles (e.g., biodegradable nanoparticles), lipsomes, micelles or any combination thereof.

In some embodiments of the present invention, the hydrogel is designed for sustained release of the factor, agent, and/or enzyme present therein. In certain embodiments, the hydrogel releases an effective amount of the factor, agent, and/or enzyme for at least about 5 days, e.g., at least about 10 days, at least about 15 days, at least about 20 days, at least about 25 days, at least about 30 days or at least about 60 days.

One of skill in the art will appreciate that the factors, agents, and enzymes discussed above with relation to certain embodiments of the present invention may likewise be included in alternate embodiments of the claimed invention. Indeed, particular embodiments of the claimed invention may incorporate factors, agents, and enzymes from each of the aforementioned categories: neural stem cell recruiting factors, neural stem cell proliferation factors, neural stem cell differentiation factors, neural stem cell mobilization factors, agents that block the biosynthesis of inhibitory ECM components, and ECM-degrading enzymes.

These and other aspects of the present invention will be discussed in more detail in the description of the invention set forth below.

BRIEF DESCRIPTION OF THE FIGURES

FIGS. 5A, 5C, 5D. Adult rat brain four weeks after focal ischemic stroke (untreated). FIGS. 5B, 5E, 5F. Adult rat brain treated with an in-situ crosslinkable hydrogel four weeks after focal ischemic stroke. FIGS. 5A-5B depict the gross morphology of the brains. FIGS. 5C, 5E contain mosaic image reconstructions of the lesions. Higher resolution images of the lesion interfaces are provided in FIGS. 5D and 5F. Light grey corresponds to GFAP staining for astrocytes. Dark grey represents Reca-1 staining for blood vessels. As shown in panel E, a well-structured vasculature network was rebuilt at the lesion injected with the in-situ crosslinkable hydrogel of the present invention.

DETAILED DESCRIPTION OF THE INVENTION

Figures 1A, 1B:
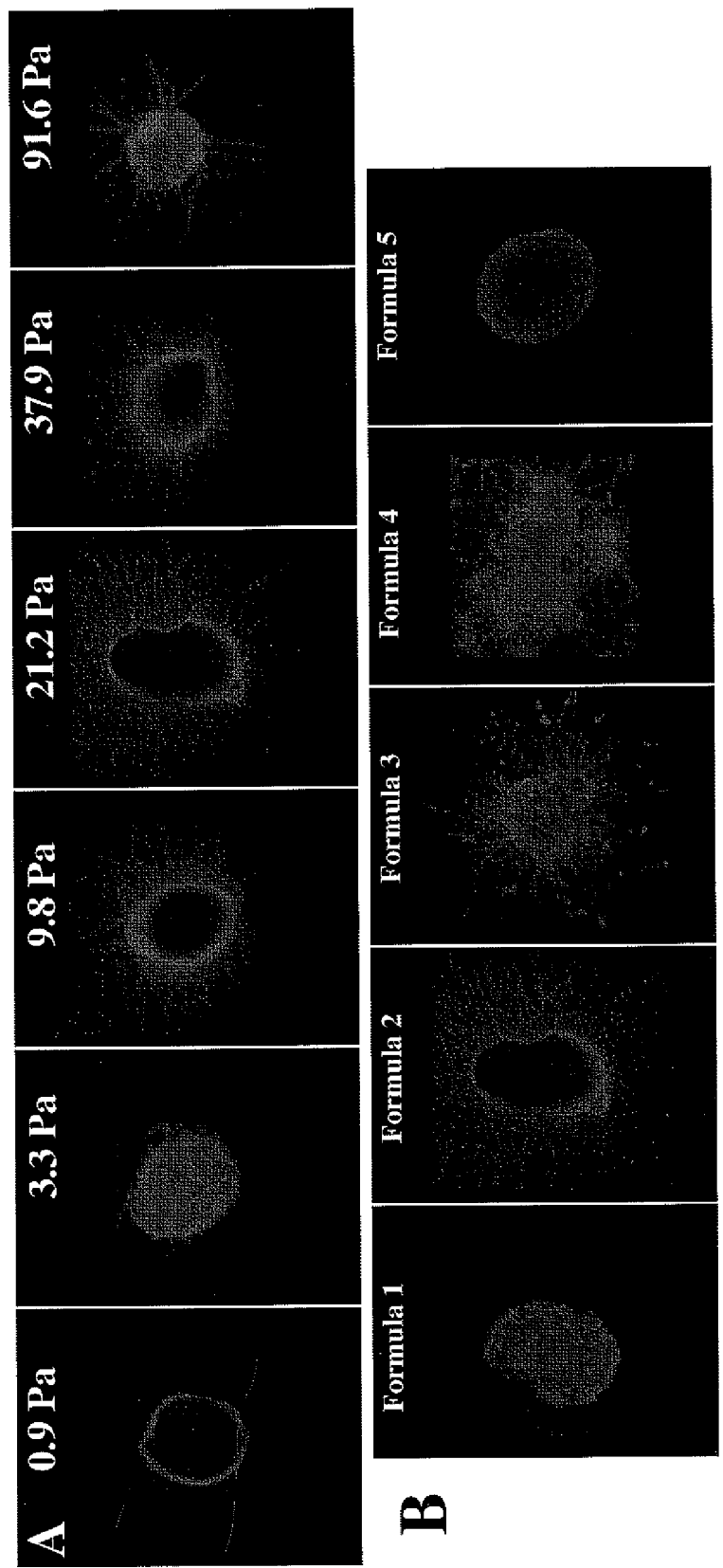
FIGS. 1A-1B show human embryonic stem cell derived neurospheres cultured inside hydrogels comprising different ratios of thiolated multi-arm PEG and laminin-derived short peptide sequences (CDPVCC GTARPGYIGSRGTARC-CAC, SEQ ID NO:1). Formula 1 is 100% PEG, Formula 2 is 75% PEG, Formula 3 is 50% PEG, Formula 4 is 25% PEG, and Formula 5 is 0% PEG.

The present invention will now be described with reference to the following embodiments. As is apparent by these descriptions, this invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference in their entirety.

DEFINITIONS

Unless indicated otherwise, explicitly or by context, the following terms are used herein as set forth below.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of 20%, 10%, 5%, 1%, 0.5%, or even 0.1% of the specified amount.

An "effective" amount as used herein is an amount of a composition of this invention that provides some improvement or benefit to the subject. Alternatively stated, an "effective" amount is an amount that provides some revascularization, reenervation, repopulation, recruitment, treatment, etc. Those skilled in the art will appreciate that such effects need not be complete or curative, as long as some benefit is provided to the subject.

By the terms "treat," "treating" or "treatment of," it is intended that the severity of the patient's condition is reduced or at least partially improved or modified and that some alleviation, mitigation or decrease in at least one clinical symptom is achieved.

As used herein, the term "in-situ crosslinkable hydrogel" describes a hydrogel of this invention in which the gelation process can occur at a local tissue site. The material components of the hydrogel can be injected into a local tissue site in the form of liquid precursors, and gelation starts at the local tissue site right after the injection. The gelation normally occurs in the presence of crosslinkers, and it is accelerated at elevated temperatures (such as at body temperatures when compared to room temperature). To control the gelation in situ, the crosslinker is mixed into the liquid precursors right before the injection so that gelation starts right after the injection. The concentration of the crosslinker in the material also determines the length of time necessary for the gelation to be completed at the tissue site.

As used herein, the term "preventing scar tissue growth in a CNS lesion" refers to any activity that effectively inhibits the growth of scar tissue in a CNS lesion, e.g., an inhibition of about 10%, 20%, 30%, 40%, 50%, 60%, 70%, 80%, 90%, 95%, or more. Those skilled in the art will appreciate that such inhibition need not be complete, as long as scar tissue growth is inhibited, e.g., in an amount that can be detected and or measured.

As used herein, the term "an agent that blocks the biosynthesis of inhibitory ECM components" refers to any molecule or compound that inhibits the biosynthesis of one or more of the molecules that comprise the ECM of scar tissue normally found in or around CNS lesion sites, e.g., an inhibition of about 10%, 20%, 30%, 40%, 50%, 60%, 70%, 80%, 90%, 95%, or more. ECM components are known to those of skill in the art, and include (but are not limited to) collagen IV and chondroitin sulphate proteoglycans. Exemplary agents include p-nitrophenyl-b-D-xylopyranoside (PNPX) and prolyl hydroxylase inhibitors (PHIS), such as ethyl-3,4 dihydroxybernoate (EDHB) and dimethyloxalylglycine (DMOG).

As used herein, the term "ECM-degrading enzyme" refers to any enzyme that promotes the breakdown and/or digestion of one or more molecules that comprise the ECM of scar tissue normally found in or around CNS lesion sites. Exemplary ECM-degrading enzymes include collagenase IV and chondroitinase ABC ($Ch^{ase}ABC$).

As used herein, the term "scar-reduced environment" refers to any environment that is substantially lacking glial scar tissue. An environment is substantially lacking glial scar tissue when less than about 20%, e.g., less than about 15%, 10%, 5%, or 1% of the total volume of the environment is occupied by glial scar tissue. Methods of measuring the total volume of a CNS lesion are known to those of skill in the art.

As used herein, the term "neural stem cell recruiting factor" refers to any molecule that promotes the attraction and/or proliferation of neural stem cells. In one embodiment, neural stem cell recruiting factors are naturally occurring proteins or active fragments or analogs thereof. Such factors include, but are not limited to, hepatocyte growth factor (HGF), insulin-like growth factor 1 (IGF-1), fibroblast growth factor 2 (FGF-2), platelet-derived growth factor (PDGF), gliotropic factors (Human recombinant annexin A2), stem cell factor-1, stromal cell-derived factor-1 (SDF-1), chemokine monocyte chemoattractant protein-1 (MCP-1, SCYA2, CCL2, MCAF), vascular endothelial growth factor (VEGF), epidermal growth factor (EGF), transmembrane protein 18 and glioma-produced ECM (tenascin-C). In other embodiments, the factor may be a small molecule, e.g., less than about 1000 Da, less than about 2000 Da, less than about 3000 Da, less than about 4000 Da less than about 5000 Da, less than about 6000 Da, less than about 7000 Da, less than about 8000 Da, less than about 9000 Da or less than about 10,000 Da.

As used herein, the term "neural differentiation factor" refers to any molecule that promotes the differentiation of neural stem cells and their precursors into neurons and/or glia. Such factors include, but are not limited to, nerve growth factor (NGF), brain-derived neurotrophic factor (BDNF), neurotrophin-3 (NT-3), neurotrophin-4 (NT-4), novel neurotrophin-1 (NNT-1), glial-cell-line-derived neurotrophic factor (GDNF), and conserved dopamine neurotrophic factor (CNTF).

As used herein, the term "neural stem cell mobilizing factor" refers to any molecule that promotes the motility of neural stem cells. Such factors include, but are not limited to, leukemia inhibitory factor (LIF) and granulocyte-colony stimulating factor (G-CSF).

I. Revascularization

Previous reports have implicated the crucial role of vasculature in inducing, supporting, and sustaining neurogenesis, neuronal survival, and brain architecture, which are fundamental for brain tissue regeneration (Ohab et al., *J. Neurosci.* 26:13007 (2006); Leventhal et al., *Mol. Cell. Neurosci.* 13:450 (1999)). Thus, reconstructing the damaged vasculature network within a CNS lesion is a fundamental step in alleviating tissue injury and promoting brain tissue regeneration.

In designing therapeutic strategies to reconstruct the damaged vasculature network of a CNS lesion, one must seek to minimize the surgical trauma to the brain tissue during the implantation procedure to protect healthy brain tissue and the integrity of the blood-brain barrier. For this purpose, biopolymer liquid precursors that are able to undergo in situ polymerization to form scaffolds that conform to the irregular dimensions of the lesion site without producing toxic residues are highly desirable.

To that end, the present invention comprises, consists essentially of, or consists of an in-situ crosslinkable hydrogel that acts as a substrate to promote angiogenesis and neural regeneration. In general, embodiments of the present invention comprise a hydrogel with mechanical properties similar to those of native CNS tissue (~10-40 Pa) and cell adhesion motifs. Most importantly, the hydrogel of the present invention is able to undergo in situ gelation in brain tissue, allowing it to conform to the irregular dimensions of the CNS lesion.

In some embodiments of the present invention, the in-situ crosslinkable hydrogel comprises at least one synthetic or ECM molecule; in other embodiments, the hydrogel comprises at least two different synthetic or ECM molecules. The synthetic molecule(s) or ECM molecule(s) may be chemically modified, such as by the addition of thiol groups or acrylate groups.

The hydrogel of the present invention may comprise any extracellular matrix molecule, including one or more of hyaluronic acid, collagen, heparin, laminin, gelatin, fibronectin, dextran, and/or chitosan. In certain embodiments, the hydrogel comprises both hyaluronic acid and collagen. In a still more preferred embodiment, the ratio of hyaluronic acid to collagen ranges from about 10:1 to about 1:10, e.g., about 5:1 to about 1:5. In one embodiment, the ratio of hyaluronic acid to collagen is about 1:3. In further embodiments, the hydrogel may comprise hyaluronic acid, collagen, and laminin.

The hydrogel of the present invention may comprise any types of PEG, including one arm PEG or multi-arm PEG. PEG may have thiol groups or acrylate groups. The hydrogel of the present invention may comprise any types of ECM derived short peptide sequences, including short peptides from collagen, laminin, gelatin, fibronectin, and so on. In certain embodiments, the hydrogel comprises both PEG and peptide sequence. In a still more preferred embodiment, the ratio of PEG to peptide sequence ranges from about 10:1 to about 1:10, e.g., about 5:1 to about 1:5. In one embodiment, the ratio of PEG to peptide sequence is about 1:3.

Importantly, the hydrogel of the present invention is capable of promoting angiogenesis in a CNS lesion without using any angiogenic growth factors. Thus, in one embodiment, the hydrogel does not comprise any angiogenic growth factors. In other embodiments, the hydrogel does comprise angiogenic growth factors. Angiogenic growth factors include, without limitation, VEGF and PDGF.

A lesion of this invention can be but is not limited to, a lesion in the brain, a lesion in the spinal cord, a lesion due to ischemia, a lesion due to hemorrhage, a lesion due to stroke, a lesion due to traumatic brain injury, a lesion due to spinal cord injury a lesion due to multiple sclerosis, as well as combinations thereof.

In some embodiments, the hydrogel of this invention can comprise at least one synthetic molecule or ECM molecule. In other embodiments, the hydrogel can comprise at least two (e.g., 2, 3, 4, 5, 6, 7, 8, 9, 10, etc.) different synthetic molecules or ECM molecules. Such synthetic or ECM molecules can be chemically modified, and/or can be thiolated and/or acrylated. In some embodiments, the hydrogel of this invention can comprise hyaluronic acid, collagen, heparin, laminin, gelatin, polyethylene glycol (in some embodiments with up to 10 arms), and/or thiolated peptide sequences as well as any combination thereof. In certain embodiments, the hydrogel of this invention comprises hyaluronic acid and collagen. In some embodiments, the ratio of hyaluronic acid to collagen can range from about 10:1 to about 1:10 (e.g., 9:1, 8:1, 7:1, 6:1, 5:1, 4:1, 3:1, 2:1, 1:1, 1:2, 1:3, 1:4, 1:5, 1:6, 1:7, 1:8, 1:9, 1:10). In particular embodiments, the ratio of hyaluronic acid to collagen ranges from about 5:1 to about 1:5 and in more particular embodiments, the ratio of hyaluronic acid to collagen is about 1:3. In other embodiments, the hydrogel can comprise hyaluronic acid, collagen and laminin. In some embodiments, the hydrogel of this invention does not comprise any angiogenic factors. In some embodiments, the hydrogel can comprise at least one neural stem cell recruiting factor, which can be, e.g., hepatocyte growth factor. In some embodiments, the hydrogel can comprise at least one mitogen (e.g., proliferating factor). In further embodiments, the hydrogel of this invention can comprise at least one neural differentiation factor, which can include but is not limited to BDNF, NT-3, GDNF and CNTF, singly or in any combination.

Some embodiments of the methods of this invention include the step comprising delivering at least one neural stem cell mobilizing factor to the CNS of a subject on whom the methods are being carried out. In particular embodiments, the neural stem cell mobilizing factor can be leukemia inhibitory factor and in some embodiments, the neural stem cell mobilizing factor can be delivered to the subventricular zone. The present invention also encompasses in the methods herein the further step comprising delivering a neural stem cell recruiting factor to a lesion site and delivering a neural stem cell mobilizing factor to the subventricular zone. In the methods described herein, the neural stem cell recruiting factor can be hepatocyte growth factor and the neural stem cell mobilizing factor can be leukemia inhibitory factor.

In the methods of this invention, the factor, agent or enzyme can be present in the hydrogel and/or can be loaded into nanoparticles, liposome's and/or micelles, in any combination. Such nanoparticles, liposome's and micelles can be biodegradable. In particular embodiments, the Nan particle can comprise PLGA or the Nan particle can be any degradable polymer.

In some embodiments, the hydrogel of this invention is designed for sustained release of the factor, agent and/or enzyme. The hydrogel can be designed for sustained release of an effective amount of the factor, agent and/or enzyme for at least 5 days, at least 30 days or at least 60 days.

In the methods described herein for preventing scar tissue growth at a CNS lesion, or maintaining a scar reduced environment in a CNS lesion, the agent that blocks the biosynthesis of inhibitory ECM components can be but is not limited to p-nitrophenyl-b-D-xylopyranoside, dimethyloxalylglycine, cyclic nucleotides, and combinations thereof.

In the methods described herein for digesting scar tissue growth in a CNS lesion or maintaining a scar reduced environment in a CNS lesion, the ECM degrading enzyme can be but is not limited to chondroitinase ABC, collagenase IV, and combinations thereof.

II. Reenervation

For the ultimate repair following cerebral stroke, neuronal and glial repopulation of the cranial lesion cavity is important. An example of a cell source for neural replacement includes endogenous neural stem cells (NSCs). These cells normally reside in the forebrain subventricular zone (SVZ)-olfactory bulb pathway in adult mammalian brain, and are able to generate neurons and glia throughout life (Gage, *Science* 287:1433 (2000)). Accumulating evidence indicates the ability of SVZ-endogenous NSCs/precursors to proliferate and migrate to areas of ischemic injury in adult brain (Jin et al., *Mol. Cell. Neurosci.* 24:171 (2003); Parent, *Neuroscientist* 9:261 (2003)). Further, NSCs are able to form appropriate neural cell types to replace damaged neurons and glia cells (Arvidsson et al., *Nature Med.* 8:963 (2002); Parent et al., *Ann. Neurol.* 52:802 (2002), suggesting that the manipulation of endogenous NSCs may be a potential strategy for brain stroke repair.

Thus, embodiments of the present invention comprise, consist essentially of, or consist of a method of delivering an in-situ crosslinkable hydrogel that contains a neural stem cell recruiting factor, mitogen/proliferation factor, and/or neural differentiation factor to the lesion in an amount effective to promote both revascularization of the lesion and recruitment of neural stem cells to the lesion. In certain embodiments, the hydrogel contains at least one neural stem cell recruiting factor and/or at least one neural differentiation factor. Neural stem cell recruiting factors suitable for use in the present invention include, but are not limited to, HGF, LIF, IGF-1, SDF-1, FGF-2, and PDGF. Neural differentiation factors suitable for use in the present invention include, but are not limited to, BDNF, NT-3, GDNF, and CNTF.

Further embodiments of the claimed invention comprise supplementing the delivery of a revascularization-promoting amount of an in-situ crosslinkable hydrogel with the delivery of a neural stem cell mobilizing factor to the CNS. In certain embodiments, the neural stem cell mobilizing factor is delivered to the subventricular zone. In other embodiments, the neural stem cell mobilizing factor can be, e.g., LIF and/or G-CSF.

Additional embodiments of the claimed invention comprise a method of delivering an in-situ crosslinkable hydrogel to a lesion in an amount effective to promote revascularization of the lesion, and delivering both a neural stem cell recruiting factor and a neural stem cell mobilizing factor to the CNS. In certain embodiments, at least one neural stem cell recruiting factor is present in the hydrogel and at least one neural stem cell mobilizing factor is delivered to the subventricular zone. In other embodiments, the neural stem cell recruiting factor is HGF and the neural stem cell mobilizing factor is LIF.

III. Scar Tissue

A detailed characterization of the cellular and biomolecular sequelae arising from ischemic stroke has led to the recognition of the predominant role of the dense ECM-rich scar tissue that forms at the lesion site in inhibiting brain tissue regeneration. Following acute focal ischemic stroke, cells undergo two major modes of deaths: necrosis, and apoptosis (Lipton, *Physiol. Rev.* 79:1431 (1999)). While necrosis is more common in the core tissue, penumbral cells that are located centrifugally from the core may undergo either mode of death. Accompanying the cell deaths, the infarcted region starts to lose structural integrity in a radial fashion from the core to the penumbra. Injured neurons and activated inflammatory cells, such as microglia, macrophages, and reactive astrocytes, may release toxic mediators at the lesion site, which amplify tissue damage (Trendelenburg et al., *Glia* 50:307 (2005)). Scattered dead neurons in the ischemic core are initially seen after 10 to 20 minutes, followed by the actual infarct formation at about 1 hour. Eventually (beyond 1-2 weeks), persistent cell dysfunction and poor neural regenerative capabilities at the ischemic core and beyond lead to the formation of a cystic cavity encapsulated in a dense layer of glial scar tissue (Lipton, *Physiol. Rev.* 79:1431 (1999)).

Scar tissue, which consists primarily of reactive astrocytes and proteoglycans (Lindsay, Reactive gliosis. In: Fedoroff S, Vernadakis A, editors. Astrocytes. Orlando: Academic Press; 1986. p 231-262), acts as a major physical barrier for brain tissue regeneration across the lesion and the structural and functional integration of the regenerating tissue with existing neural circuitry (Lipton, *Physiol. Rev.* 79:1431 (1999); Gartshore et al., *Exp. Neurol.* 147:353 (1997)). In addition, scar tissue may serve as a diffusion barrier, obstructing the delivery of pharmacological agents and the transport of oxygen and nutrients to cells implanted within the lesion cavity.

In the acute and subacute stages of stroke, inflammatory cells travel from the vasculature into the ischemic region, and interact to form a dense structure known as a glial scar. The response of astrocytes to injury is characterized by hypertrophy and hyperplasia (Barrett et al., *Exp. Neurol.* 84:374 (1984)), accompanied by an increased production of intermediate filaments (such as GFAP (Bignami et al., *J. Comp. Neurol.* 153:27 (1974); Eng, *J. Neuroimmunol.* 8:203 (1985)) and vimentin (Yang et al., *Mol. Chem. Neuropathol.* 21:155 (1994))). In addition, astrocytes—along with other CNS-resident cells, such as microglia and oligodendrocytes, and hematogenous cells, like macrophages—play a role in the regulation of ECM production after CNS injury (Fitch et al., *J. Neurosci.* 19:8182 (0.1999); Preston et al., *J. Neurotrauma* 18:83 (2001)). The resulting ECM contains several classes of molecules that are inhibitory to brain tissue regeneration, including proteoglycans (Gallo et al., *Exp. Cell Res.* 187:211 (1990); Gallo et al., *Dev. Biol.* 123:282 (1987)), collagen type IV (Hermanns et al., *Restor. Neurol. Neurosci.* 19:139 (2001); Hermanns et al., *J. Neurosci. Meth.* 110:141 (2001); Stichel et al., *Eur. J. Neurosci.* 11:632 (1999)), and the basal membrane (Lips et al., *J. Neurocytol.* 24:449 (1995); Stichel et al., *J. Neurocytol.* 23:615 (1994); Stichel et al., *Eur. J. Neurosci.* 7:401 (1995); Timpl et al., *Int. Rev. Exp. Pathol.* 29:1 (1986)).

Proteoglycans represent a special class of heavily glycosylated glycoproteins characterized by a protein core that is covalently linked by four sugar moieties to a sulphated glycosaminoglycan (GAG) chain. Among the four types of proteoglycans (Johnson-Green et al., *Glia* 4:314 (1991)), the chondroitin sulphate proteoglycans (CSPGs) are a relatively large family. Up-regulation of CSPG production has been documented in glial scars in both the brain and spinal cord of adult mammalians (Jones et al., *Exp. Neurol.* 182:399 (2003); McKeon et al., *J. Neurosci.* 19:10778 (1999); Tang et al., *J. Neurosci. Res.* 71:427 (2003)). The inhibitory effects of CSPGs on axonal outgrowth and CNS tissue regeneration have been demonstrated both in vitro (Hynds et al., *Exp. Neurol.* 160:244 (1999); Snow et al., *Exp. Neurol.* 109:111 (1990)) and in vivo (Jones et al., *J. Neurosci.* 22:2792 (2002); Moon et al., *Neuroscience* 109:101 (2002)), suggesting that elimination of these ECM molecules may be essential to promote CNS tissue repair and regeneration.

In addition to the inhibitory effects of CSPGs, several other molecules are known to be up-regulated in the glial scar and to contribute to regeneration failure. Collagen IV, a matrix molecule that is primarily secreted by meningeal fibroblasts, is a major component of the basal membrane, and has been implicated in the inhibition of regeneration after CNS injury (Klapka et al., *J. Neurotrauma* 23:422 (2006)). In a brain lesion model of post-commissural formix transaction, collagenous basal membrane was shown to be a major impediment for axon regeneration (Hermanns et al., *Restor. Neurol. Neurosci.* 19:139 (2001)). Blocking collagen IV deposition promoted axonal regeneration across the lesion site following mechanical injury to adult rat brain (Stichel et al., *Eur. J. Neurosci.* 11:632 (1999)).

Since any form of treatment designed to regenerate brain tissue after stroke, TBI, or SCI will have to occur at the lesion site, sustaining a scar-reduced, permissive environment is key to successful brain tissue regeneration. To that end, the present invention provides methods of preventing scar tissue growth in a CNS lesion, digesting existing scar tissue in a CNS lesion, and maintaining a scar-reduced environment in a CNS lesion.

Selective enzymatic removal of ECM molecules from glial scar tissue results in the degradation of pre-existing scars within the CNS lesion (Zuo et al., *J. Neurosci.* 18:5203 (1998); Zuo et al., *Exp. Neurol.* 154:654 (1998)), thereby enhancing CNS repair. For example, chondroitinase ABC ($Ch^{ase}ABC$) may be used to digest the GAG moieties of CSPGs, resulting in the dissolution of pre-existing scar tissue and enhanced axonal regeneration (Snow et al., *Exp. Neurol.* 109:111 (1990); Bradbury et al., *Nature* 416:636 (2002); Moon et al., *Nature Neurosci.* 4:465 (2001); Li et al., *J. Neurosci. Res.* 85:536 (2007)). Likewise, the degradation of collagen IV quells the lesion-induced deposition of basal membrane and partially facilitates CNS tissue regeneration (Stichel et al., *Eur. J. Neurosci.* 11:632 (1999); Guth et al., *J. Neurosurg.* 52:73 (1980)).

Thus, some embodiments of the present invention comprise a method of delivering to a lesion an amount of an in-situ crosslinkable hydrogel comprising at least one ECM-degrading enzyme, wherein said amount is effective to digest scar tissue. Appropriate enzymes may include, without limitation and in any combination, CSPG-digesting enzymes, such as $Ch^{ase}ABC$, and collagen-eliminating enzymes, such as collagenase IV. In certain embodiments, the ECM-based hydrogel comprises both $Ch^{ase}ABC$ and collagenase IV.

In addition to digesting pre-existing glial scar tissue, it is desirable to prevent the formation of new scar tissue in the lesion site. The formation of new scar tissue can be prevented by blocking the biosynthesis of repair-inhibiting ECM molecules. Several compounds have been found to be useful in the present invention to inhibit scar formation, including CSPG suppressors such as p-nitrophenyl-b-D-xylopyranoside (PNPX) (Zhang et al., World Congress on Tissue Engineering and Regenerative Medicine (2006) Pittsburgh, Pa., presented Apr. 27, 2006), and prolyl hydroxylase inhibitors (PHIs), such as ethyl-3,4 dihydroxybenzoate (EDHB) and dimethyloxalylglycine (DMOG) (Zhang et al., Abstracts of Papers of the American Chemical Society 229:U911 (2005) San Diego, Calif., presented Mar. 13, 2005), which notably inhibit collagen IV synthesis. In addition, it is known that cyclic nucleotides are able to convert myelin-associated glycoproteins from an axon-repulsive state to one in which they attract axonal outgrowth.

Thus, embodiments of the present invention comprise a method of delivering to a lesion an amount of an in-situ crosslinkable hydrogel comprising at least one agent that blocks the biosynthesis of inhibitory ECM components, wherein said amount is effective to prevent scarring. Appropriate agents include those that block the biosynthesis of CSPG, such as PNPX, agents that block the biosynthesis of collagen IV, such as EDHB and DMOG, and cyclic nucleotides as well as any combination thereof. In certain embodiments, the in-situ crosslinkable hydrogel comprises at least one agent that blocks the biosynthesis of CSPG and at least one agent that blocks the biosynthesis of collagen IV.

Further embodiments of the present invention are aimed at maintaining a scar-reduced lesion site. These embodiments comprise a method of delivering to a lesion an amount of an in-situ crosslinkable hydrogel comprising at least one agent that blocks the biosynthesis of inhibitory ECM components and, optionally, at least one ECM-degrading enzyme, wherein said amount is effective to maintain a scar-reduced environment. Certain embodiments comprise an in-situ crosslinkable hydrogel that contains agents that block the biosynthesis of CSPG and collagen IV, as well as the enzymes $Ch^{ase}ABC$ and collagenase IV, in any combination.

Given the ubiquitous nature of CSPGs and collagen IV within the CNS, one skilled in the art will appreciate the need to carefully control the release of enzymes and/or agents that interfere with the normal life cycle of these ECM components. The present invention provides for such control via the slow, sustained release of ECM-degrading enzymes and biosynthesis-blocking agents within the lesion, with the release rate controlled by the composition (e.g., density, charge, shape) of the hydrogel.

Further embodiments of the present invention comprise in-situ crosslinkable hydrogels wherein the factor, agent, and/or enzyme contained therein is present as a nanoparticle. In certain embodiments, the factor, agent, and/or enzyme will be loaded into a biodegradable nanoparticle, such as PLGA, liposomes, micelles, and/or any other suitable degradable polymers, as are well known in the art.

The hydrogels of this invention can further comprise a polyalkylene glycol (PAG) moiety, which is some embodiments can be poly(ethylene glycol) (PEG). The PAG or PEG can have a molecular weight in the range of about 10,000 to about 40,000. The PEG of this invention can be single arm or multi-arm (e.g., 1, 2, 3, 4, 5, 6, 7, 8, 9, or 10 arms, etc.) PEG.

"Polyalkylene glycol" means straight or branched polyalkylene glycol polymers including, but not limited to, polyethylene glycol (PEG), polypropylene glycol (PPG), and polybutylene glycol (PBG), as well as co-polymers of PEG, PPG and PBG in any combination, and includes the monoalkylether of the polyalkylene glycol. Thus, in various embodiments of this invention, the polyalkylene glycol in the compositions of this invention can be, but is not limited to, polyethylene glycol, polypropylene glycol, polybutylene glycol, and any combination thereof.

In certain embodiments, the polyalkylene glycol of the composition is polyethylene glycol or "PEG." The term "PEG subunit" refers to a single polyethylene glycol unit, i.e., —($CH_2CH_2O$)—.

In some embodiments, the polyalkylene glycol (e.g., PEG) can be non-polydispersed, monodispersed, substantially monodispersed, purely monodispersed, or substantially purely monodispersed.

"Monodispersed" is used to describe a mixture of compounds wherein about 100 percent of the compounds in the mixture have the same molecular weight.

"Substantially monodispersed" is used to describe a mixture of compounds wherein at least about 95 percent of the compounds in the mixture have the same molecular weight.

"Purely monodispersed" is used to describe a mixture of compounds wherein about 100 percent of the compounds in the mixture have the same molecular weight and have the same molecular structure. Thus, a purely monodispersed mixture is a monodispersed mixture, but a monodispersed mixture is not necessarily a purely monodispersed mixture.

"Substantially purely monodispersed" is used to describe a mixture of compounds wherein at least about 95 percent of the compounds in the mixture have the same molecular weight and have the same molecular structure. Thus, a substantially purely monodispersed mixture is a substantially monodispersed mixture, but a substantially monodispersed mixture is not necessarily a substantially purely monodispersed mixture.

The present invention is explained in greater detail in the following non-limiting examples.

Example 1

Composition of Synthetic Hydrogels

FIGS. 1A-1B show human embryonic stem cell derived neurospheres cultured in hydrogels comprising different ratios of 4-Arm PEG and short peptide sequence (CDPVCC GTARPGYIGSRGTARCCAC, SEQ ID NO:1). While all of the hydrogels supported growth of the cells, a PEG:peptide ratio of 25:75 produced the best results.

Example 2

Figure 2A:
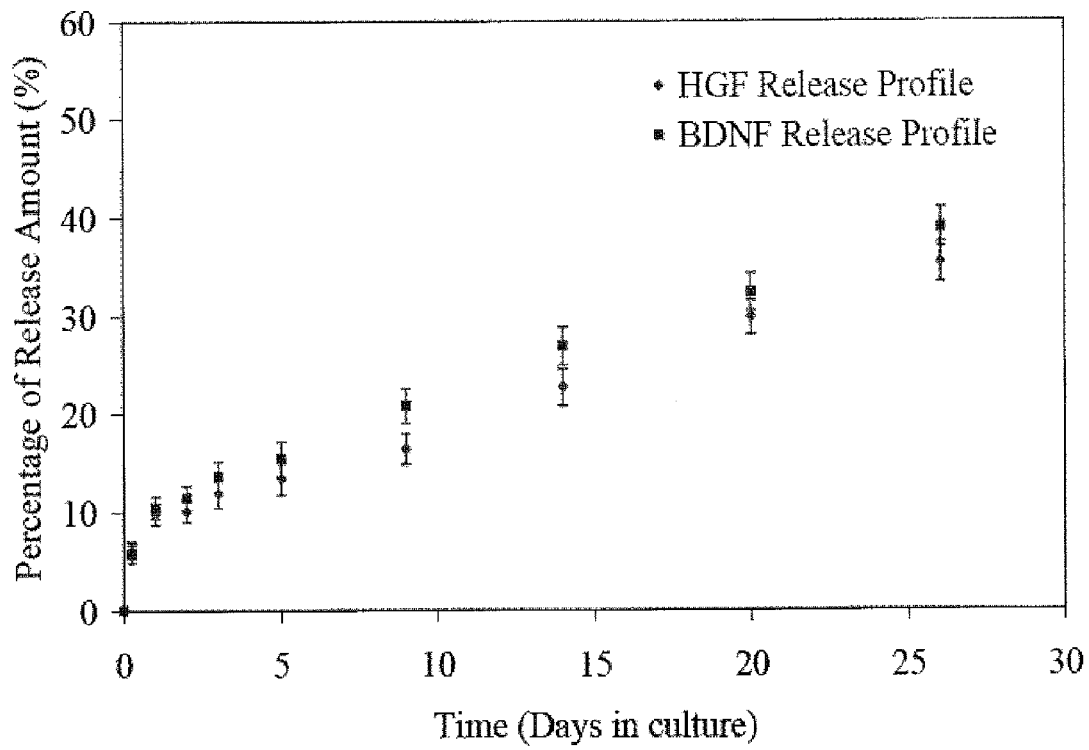
FIGS. 2A-2B show sustained release of biologically active molecules from an ECM-based hydrogel.
Figure 2B:
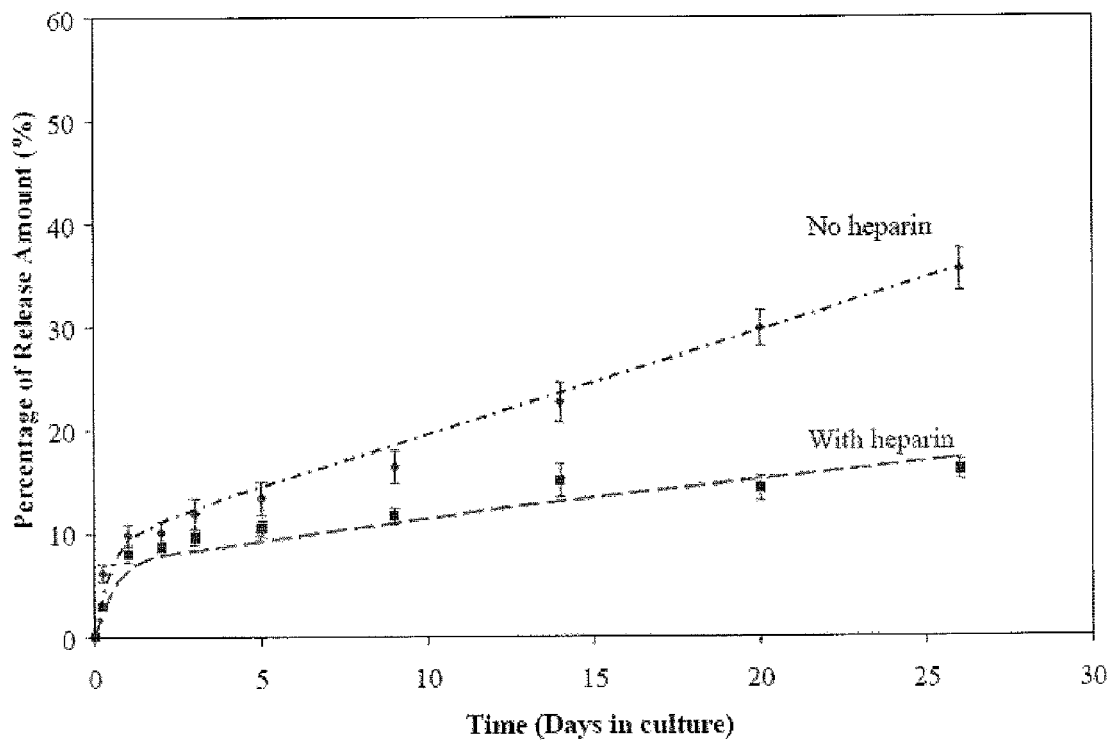
Figure 2C:
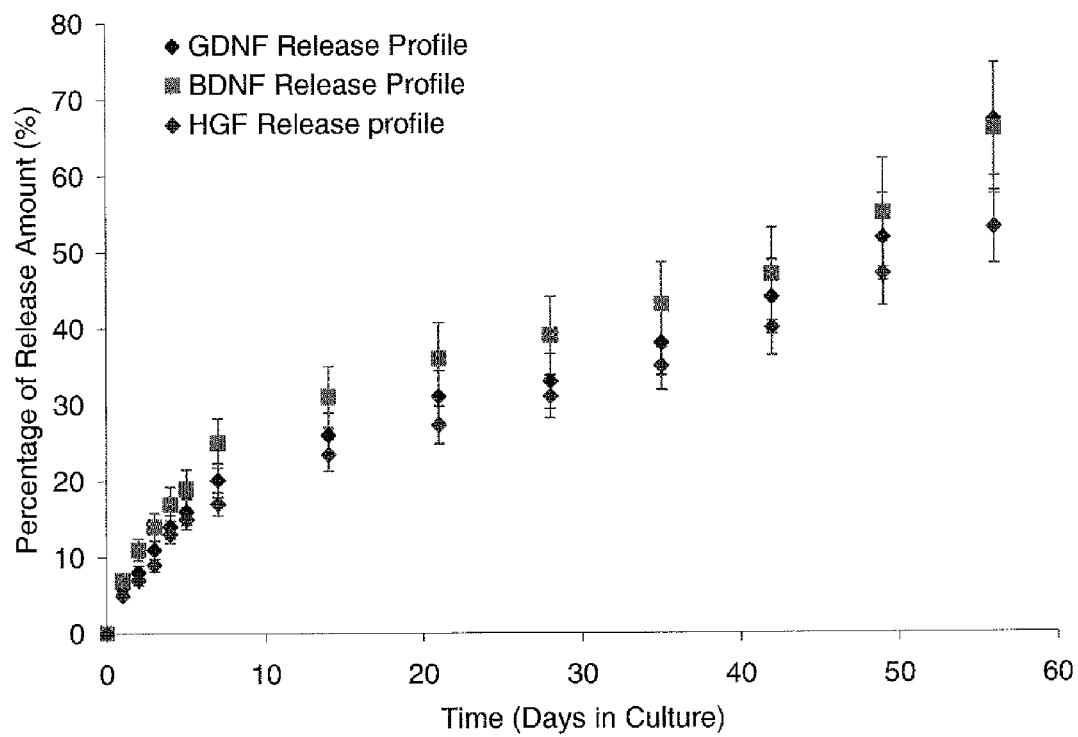
FIG. 2C shows sustained release of biological active molecules from 4-arm thiolated PEG and thiolated laminin short peptide based hydrogel. Cumulative in vitro GDNF, BDNF and HGF release from the synthetic hydrogel is measured. After 1 and 2 months, about 35% and 70%, respectively, of the growth factors are released.

Sustained Release of Biologically Active Molecules from In-Situ Crosslinkable Hydrogels FIGS. 2A-C show sustained release of biologically active molecules from an ECM-based hydrogel. (A) Cumulative in vitro HGF and BDNF release from an ECM-based hydrogel comprising hyaluronic acid and collagen. After 26 days, approximately 35-40% of each growth factor was released from each hydrogel. (B) Cumulative in vitro HGF release from ECM-based hydrogels comprising hyaluronic acid and collagen (circles), or hyaluronic acid, collagen and heparin (squares). Addition of heparin in HA-collagen hydrogel doubles the release duration of HGF from the hydrogels. The hydrogel provides sustained release of biologically active growth factor in vitro, with release sustained for 3-6 months. This is a dramatic increase in time of availability compared to the short half-life of free growth factors in vivo. (C) Cumulative in vitro GDNF, BDNF and HGF release from the synthetic hydrogel. After 1 and 2 months, about 35% and 70%, respectively, of the growth factors are released.

Example 3

Attracting Stem Cells In Vitro and In Vivo

Figures 3A, 3B:
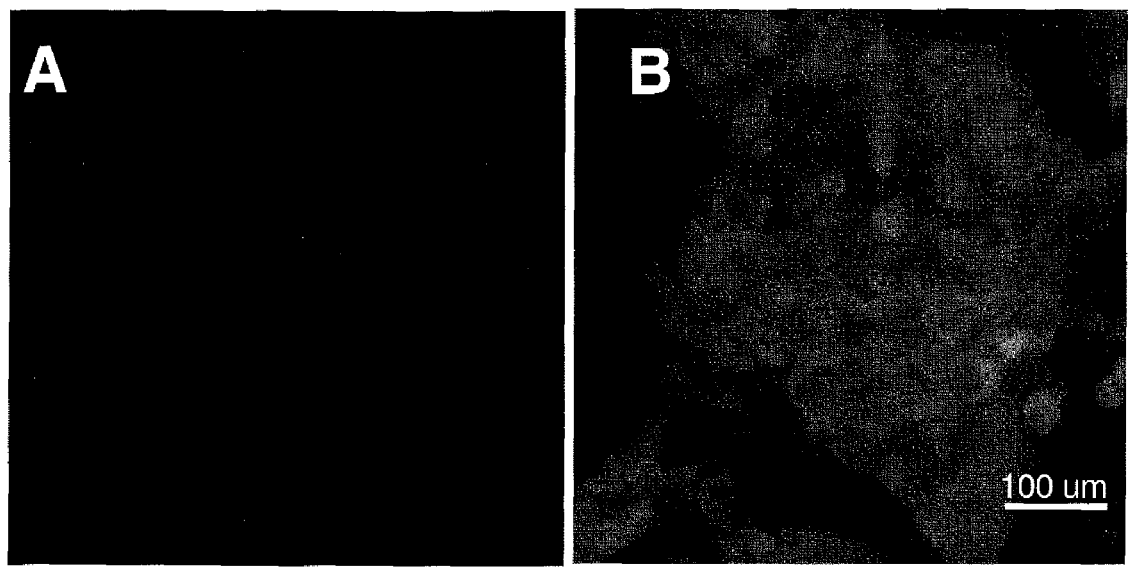
FIGS. 3A-3B show recruitment of stem cells to hydrogels containing hepatocyte growth factor in vitro. Sustained and localized release of HGF from hydrogels (B) is able to induce neural stem cell migration and recruitment into the hydrogel. Dark grey is staining for cell nuclei; black spotting is neurofilament staining, and light grey is nestin staining for neural stem cells. (A) is no HGF control.
Figure 4A:
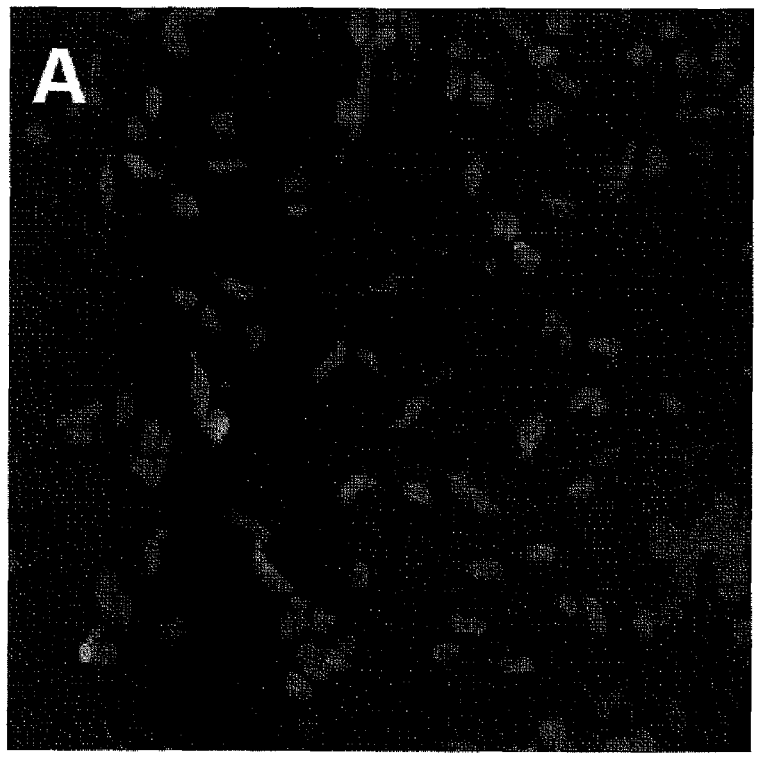
FIGS. 4A-4D show recruitment of endogenous stem cells to hydrogels containing hepatocyte growth factor. ECM-based hydrogels loaded with (A) control or (B) HGF were implanted into the subcutaneous space on the back of mice. Hydrogels were harvested 1 week after implantation, and samples of each were stained. C. Quantitative analysis of the total number of cells that migrated into control and HGF-containing hydrogels. D. HGF-loaded hydrogel stained with anti-STRO-1 following 1 week incubation in the subcutaneous space on the back of as mouse.
Figure 4B:
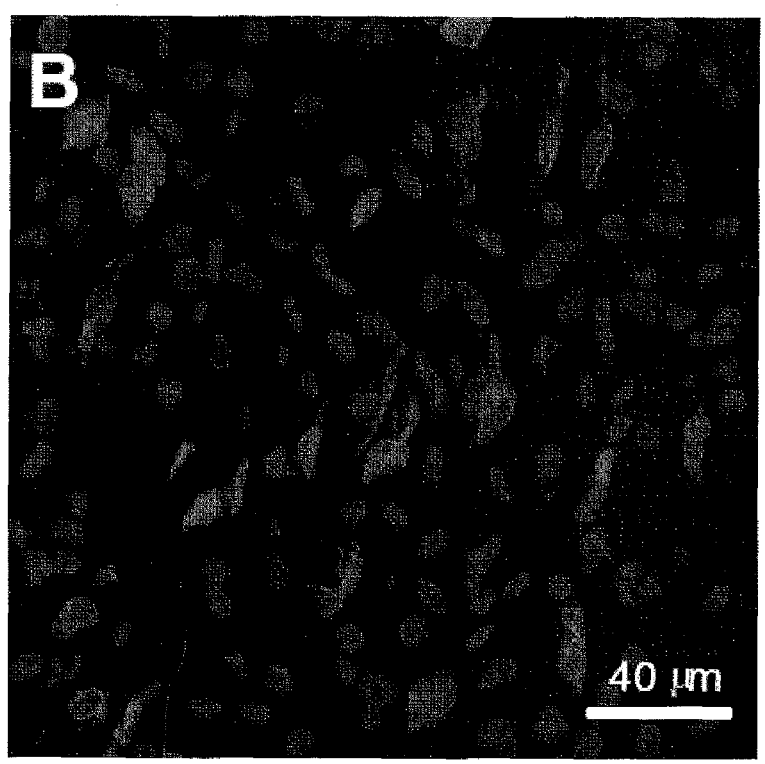
Figure 4C:
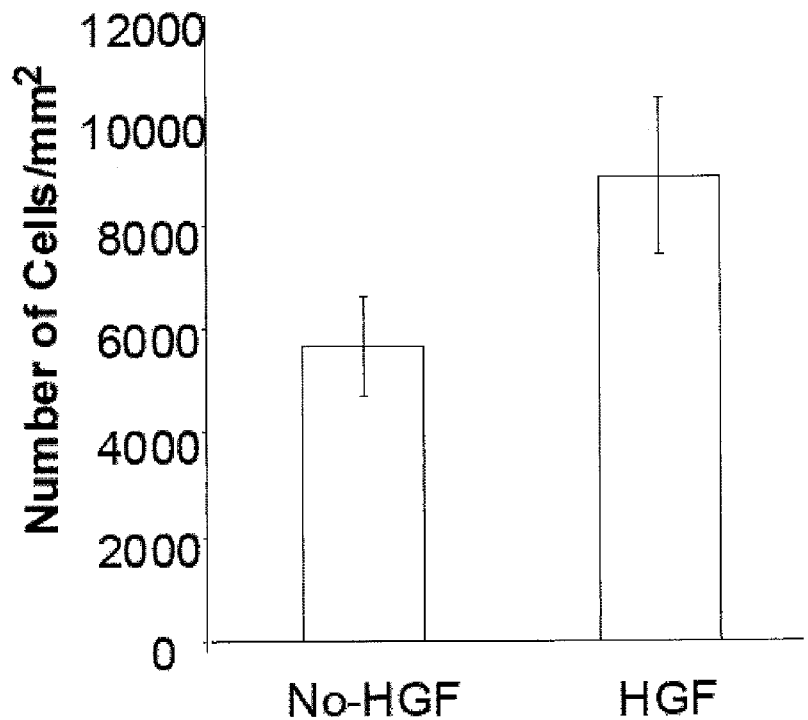
Figure 4D:
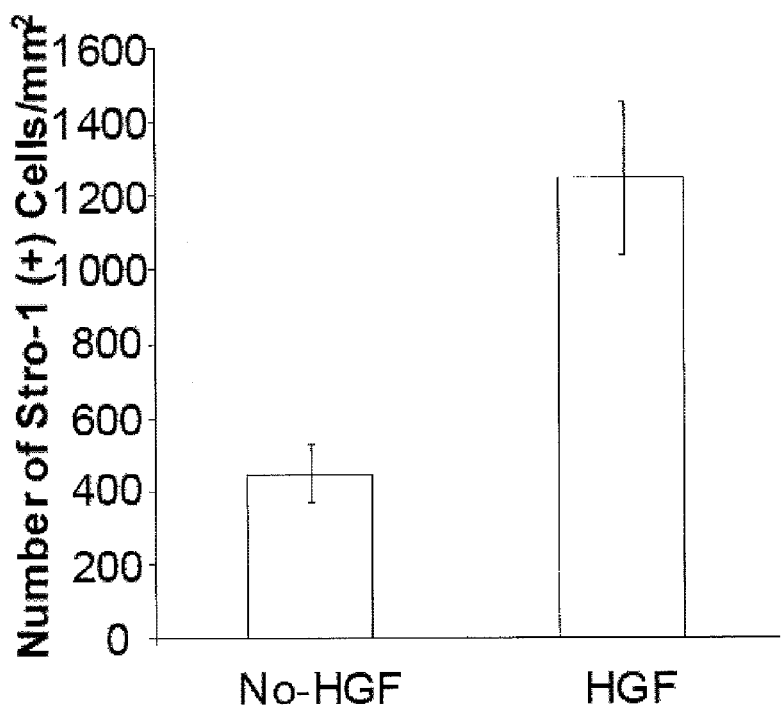
Figure 5A:
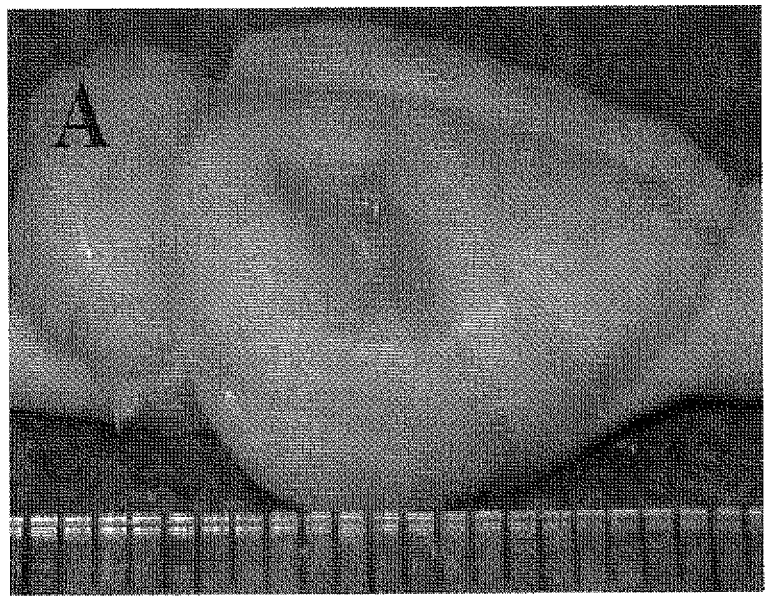
FIGS. 5A-5F show revascularization of a CNS lesion with injection of in-situ crosslinkable hydrogel following stroke.
Figure 5B:
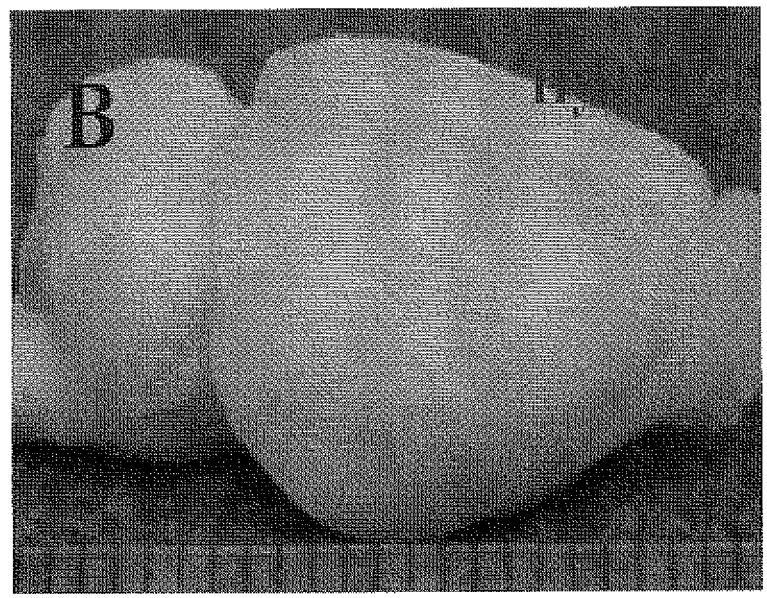
Figures 5C, 5D, 5E, 5F:
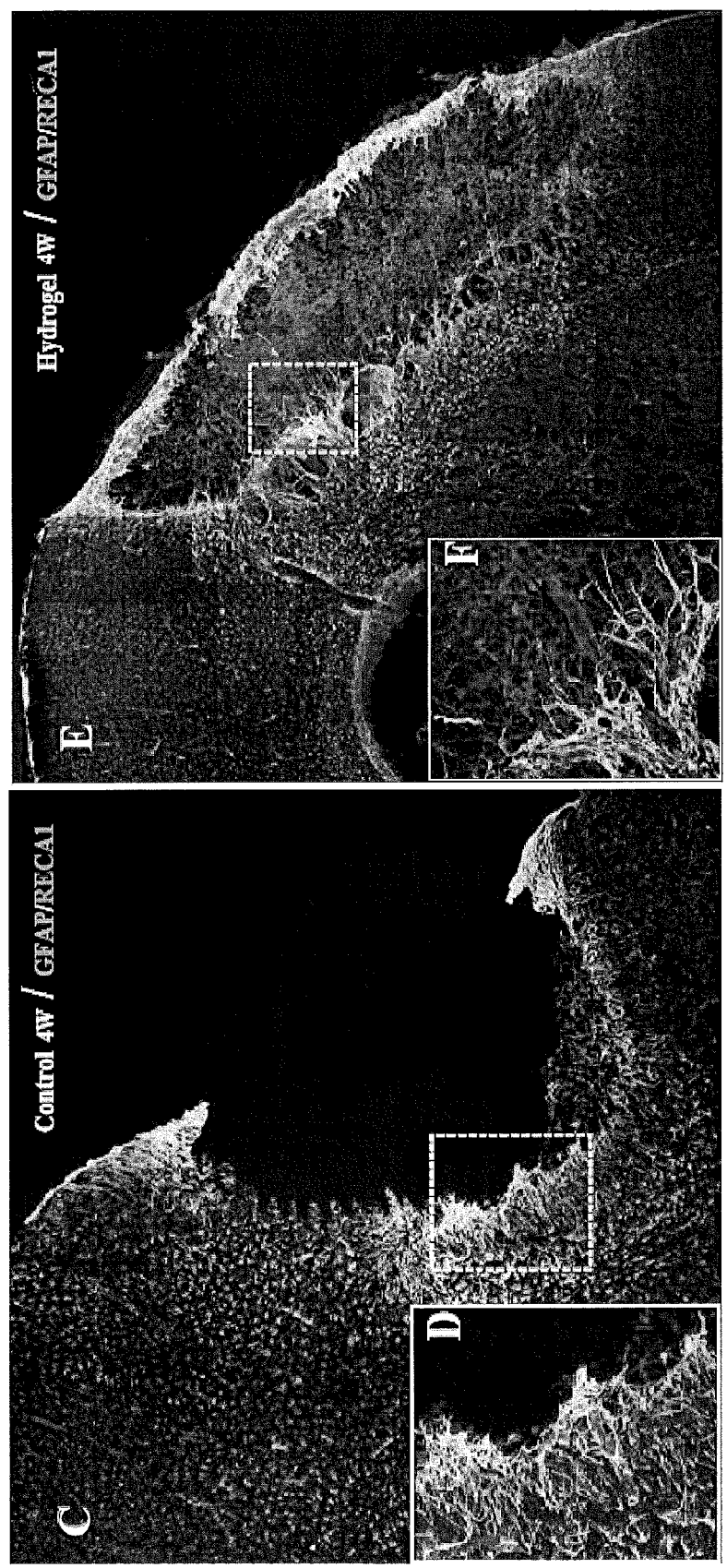
Figures 6A, 6B, 6C, 6D, 6E:
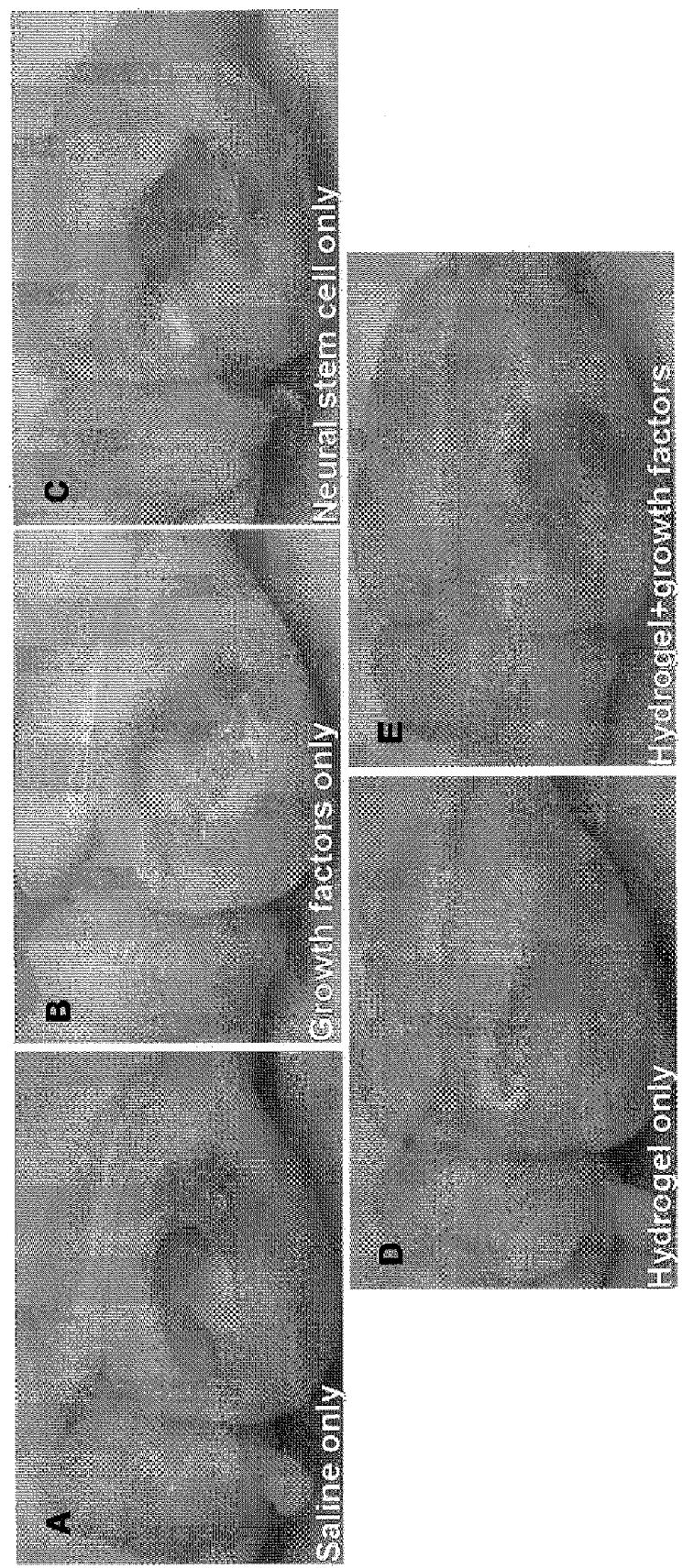
FIGS. 6A-6E show different outcomes after TBI. (A) Cavity formed at the lesion site 8 weeks after saline injection at the 3rd day after traumatic brain injury (TBI). (B) Cavity formed at the lesion site 8 weeks after direct injection of growth factors (HGF, GDNF, BDNF, FGF2) without using hydrogels. (C) Cavity formed at the lesion site 8 weeks after direct injection of neural stem cells without using hydrogels. (D) No cavity formation was found 8 weeks after hydrogel injection at the 3rd day after traumatic brain injury (TBI). (E) No cavity formation was found 8 weeks after injection of growth factors (HGF, GDNF, BDNF, FGF2) loaded in hydrogel at the 3rd day after traumatic brain injury (TBI).

FIGS. 3A-B show recruitment of stem cells to in-situ crosslinkable hydrogels containing hepatocyte growth factor (HGF). Neural stem cells ($5\times10^3$ in 200 µl culture media) were added to the upper compartment of a transwell. The lower compartment was filled with 400 µl of culture medium and an in-situ crosslinkable hydrogel as control (A), or an in-situ crosslinkable hydrogel containing 80 ng/ml solubilized HGF (B). Hydrogels were harvested following an 8-hour incubation period and stained. Sustained and localized release of HGF from the hydrogel (B) is able to induce neural stem cell migration and recruitment into the hydrogel.

FIGS. 4A-D show recruitment of endogenous stem cells to ECM-based hydrogels containing hepatocyte growth factor (HGF). ECM-based hydrogels loaded with control (A) or HGF (B) were implanted into the subcutaneous space on the back of mice. Hydrogels were harvested 1 week after implantation, and samples of each were stained. (C) Quantitative analysis of the total number of cells that migrated into control and HGF-containing hydrogels. (D) HGF-loaded hydrogel stained with anti-STRO-1 following 1 week incubation in the subcutaneous space on the back of as mouse.

Example 4

Stroke Animal Model

FIGS. 5A-F show revascularization of a CNS lesion following stroke. (A, C, D) Adult rat brain four weeks after focal ischemic stroke (untreated). (B, E, F) Adult rat brain treated with an in-situ crosslinkable hydrogel four weeks after focal ischemic stroke. A and B depict the gross morphology of the brains. C and E contain mosaic image reconstructions of the lesions. Higher resolution images of the lesions interfaces are provided in D and F. As shown in panel E, a well-structured vasculature network was rebuilt at the lesion injected with the in-situ crosslinkable hydrogel of this invention.

Example 5

TBI Animal Model

FIGS. 6A-E show different outcomes after TBI. (A) Cavity formed at the lesion site 8 weeks after saline injection at the 3rd day after traumatic brain injury (TBI). (B) Cavity formed at the lesion site 8 weeks after direct injection of growth factors (HGF, GDNF, BDNF, FGF2) without using hydrogels. (C) Cavity formed at the lesion site 8 weeks after direct injection of neural stem cells without using hydrogels. (D) No cavity formation was found 8 weeks after hydrogel injection at the 3rd day after traumatic brain injury (TBI). (D) No cavity formation was found 8 weeks after injection of growth factors (HGF, GDNF, BDNF, FGF2) loaded in hydrogel at the 3rd day after traumatic brain injury (TBI).

Example 6

Endogenous Neural Stem Cell Recruitment

Figures 7A, 7B:
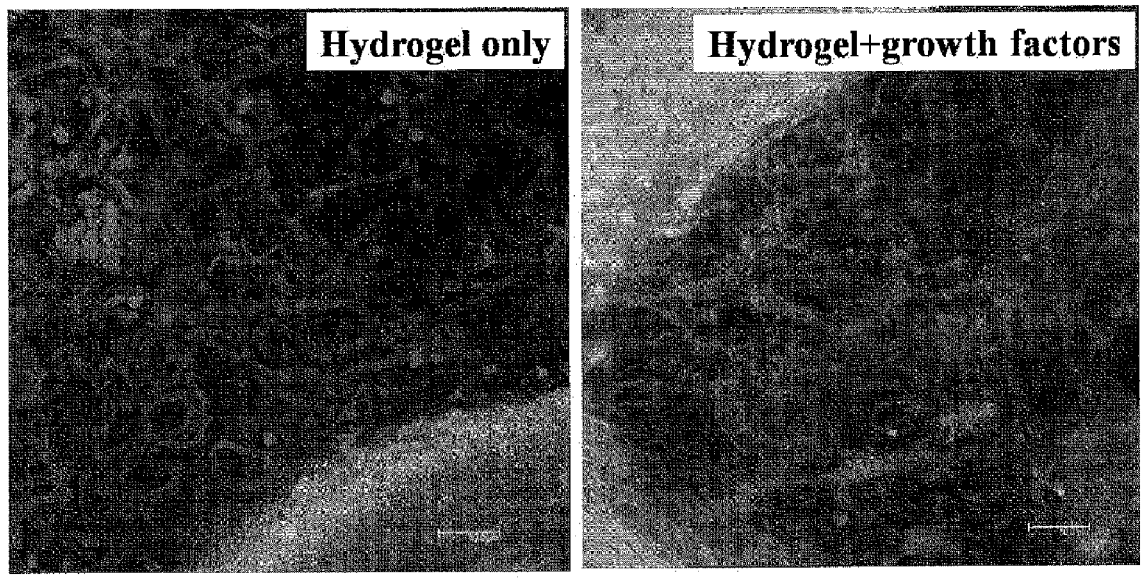
FIGS. 7A-7B. Neural regeneration after hydrogel injection. (A) There is robust vascular formation (light grey), but no neuronal regeneration in the TBI lesion site after only hydrogel injection without the use of growth factor cocktail. (B) There is robust vascular formation and neuronal regeneration (very light grey) after growth factor cocktail (HGF, FGF2, GDNF, BDNF) loaded hydrogel injection.

FIGS. 7A-B show neural regeneration after hydrogel injection. (A) There is robust vascular formation, but no neuronal regeneration in the TBI lesion site after only hydrogel injection without the use of the growth factor cocktail. (B) There is robust vascular formation and neuronal regeneration after growth factor cocktail (HGF, FGF2, GDNF, BDNF)-loaded hydrogel injection.

Example 7

Carrier for Transplantation

Figures 8A, 8B:
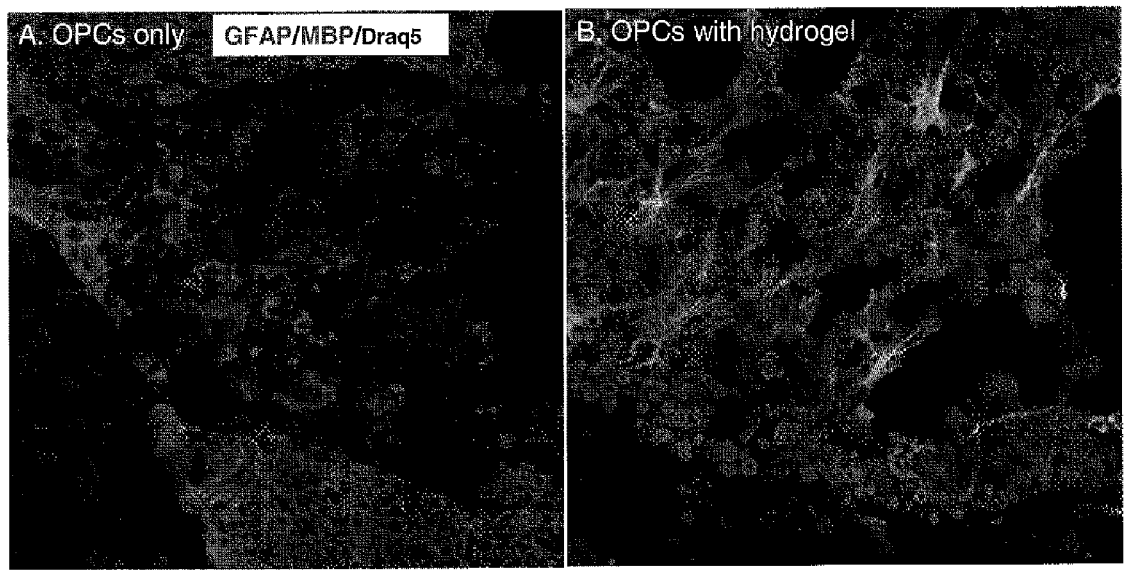
FIGS. 8A-8B. Four weeks after oligodendrocytes precursor cells (OPCs) transplanted into the ethidium bromide localized lesion rat spinal cord. (A) OPC only and (B) OPC transplanted with the hydrogel. Light grey is MBP (myelin basic protein) staining for differentiated oligodendrocytes. Very light grey is GFAP staining for astrocytes and dark grey is Draq-5 staining for cell nuclei. As shown in (B), more functionally viable oligodendrocytes and more myelination are seen in the hydrogel groups.
Figure 9A:
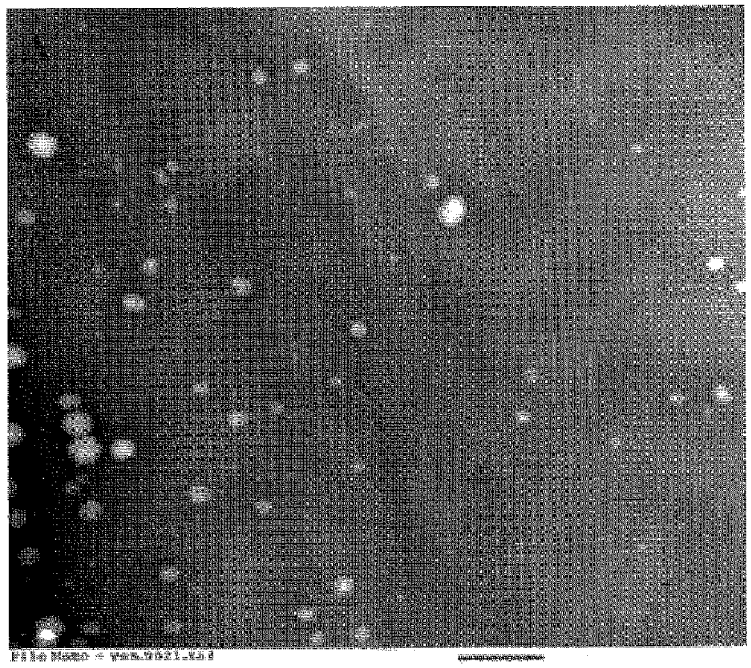
FIGS. 9A-9D. Inhibition of collagen IV biosynthesis using dimethyloxalylglycine (DMOG) nanoparticles. (A) Degradable nanoparticles loaded with DMOG. (B) Size distribution of DMOG-loaded nanoparticles (average size=45 nm). (C) Nanoparticles stained with anti-collagen IV antibody 4 weeks after the implantation of control nanoparticles. (D). nanoparticles containing DMOG. Scale bar=75 um. Dotted lines indicate the borders of implanted hollow fibers.
Figure 9B:
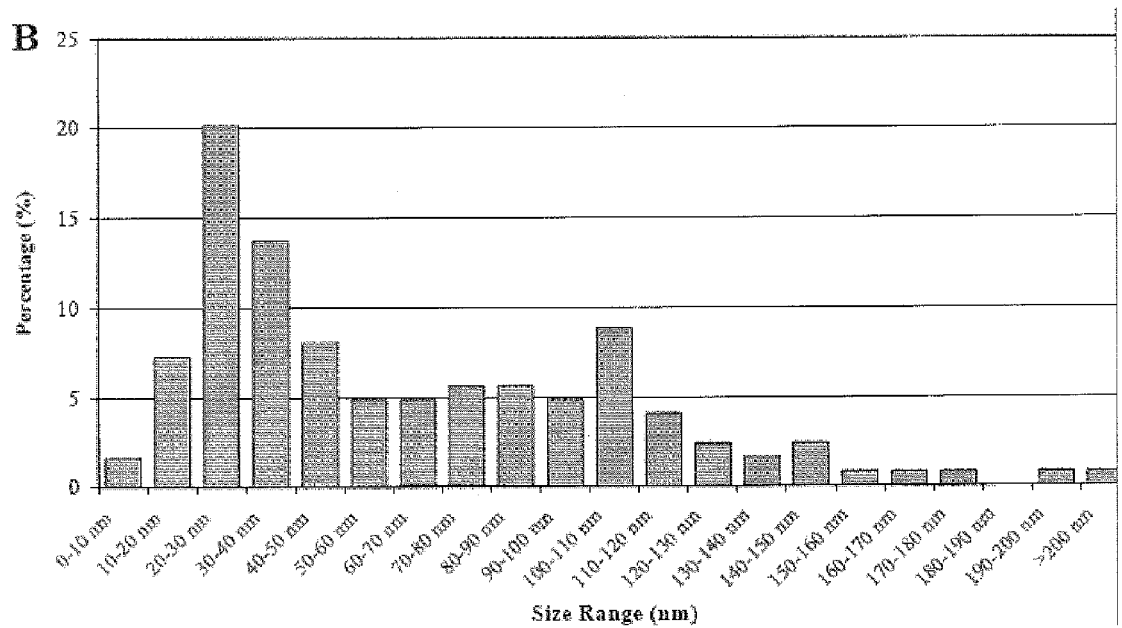
Figures 9C, 9D:
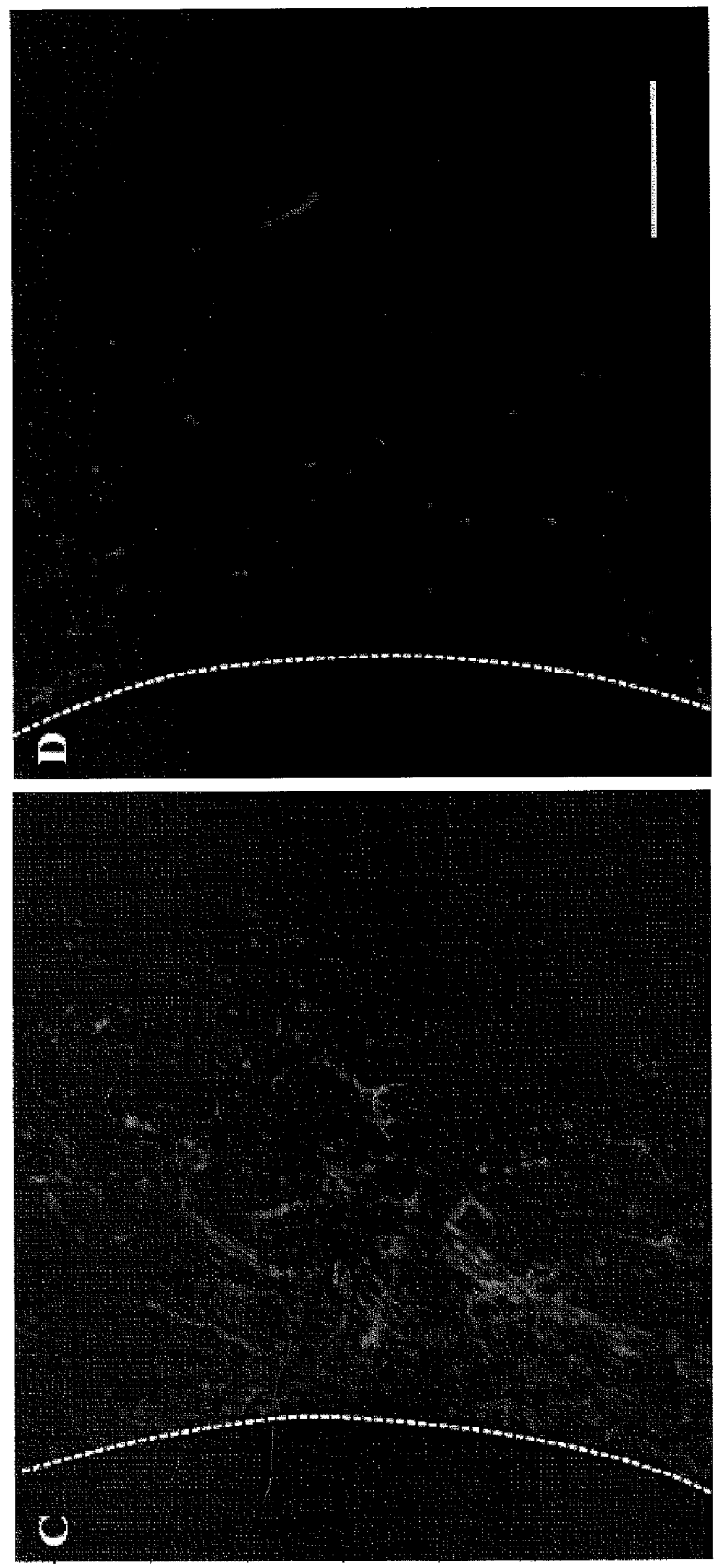

Myelin is damaged in many diseases, such as multiple sclerosis (MS) and leukodystrophies. Myelin is also destroyed in neural tissue injury, such as spinal cord injury (SCI) and traumatic brain injury (TBI). Remyelination has to occur in order to cure these diseases and is also the key step to fully regenerate injured spinal cord or brain tissue. At present, there are no effective therapies in the clinic that promote remyelination. There is growing evidence that exogenous cell transplantation is one promising strategy to promote remyelination. However, direct injection of neural stem cells or oligodendrocyte precursor cells (OPCs) to the lesion site may not be an optimal therapeutic strategy since the viability and functionality of transplanted cells are compromised by the local hostile environment, e.g., in MS disease sites. There is an urgent need to find effective strategies to improve remyelination. In order to improve the viability of the transplanted cells, the microenvironments of the diseased tissue has to be re-conditioned for transplanted cells to survive. One way to manipulate the local microenvironment is to use an injectable neural biocompatible hydrogel system loaded with factors to provide a regeneration permissive microenvironment. To this end, hydrogels made of multi-arm polyethylene glycol (PEG) and modified short laminin peptide sequence were used as a carrier for cell transplantation. These hydrogel systems support remyelination. FIG. 8 shows that increased myelination occurred when OPCs are transplanted with these hydrogels (FIG. 1).

Example 8

Nanoparticles

FIGS. 9A-D show inhibition of collagen IV biosynthesis using dimethyloxalylglycine (DMOG) nanoparticles. (A) Degradable nanoparticles loaded with DMOG. (B) Size distribution of DMOG-loaded nanoparticles (average size=45 nm). (C, D) Nanoparticles stained with anti-collagen IV antibody 4 weeks after the implantation of control nanoparticles (C) or nanoparticles containing DMOG (D). Scale bar=75 um. Dotted lines indicate the borders of implanted hollow fibers.

The foregoing is illustrative of the present invention, and is not to be construed as limiting thereof. The invention is defined by the following claims, with equivalents of the claims to be included therein. All publications, patent applications, patents, patent publications, and any other references cited herein are incorporated by reference in their entireties for the teachings relevant to the sentence and/or paragraph in which the reference is presented.

prises thiolated hyaluronic acid, thiolated polyethylene glycol and a thiolated laminin peptide sequence comprising the amino acid sequence CDPVCCGTARPGYIGSRGTARCCAC (SEQ ID NO:1).

6. A method of repopulating a CNS lesion with functional neural cells, comprising delivering to the lesion an amount of a hydrogel comprising a neural stem cell recruiting factor, wherein said amount is effective to promote revascularization of the lesion and repopulation of the lesion with functional neural cells, wherein the hydrogel comprises thiolated hyaluronic acid, thiolated polyethylene glycol and a thiolated laminin peptide sequence comprising the amino acid sequence CDPVCCGTARPGYIGSRGTARCCAC (SEQ ID NO:1).

7. The method of claim 6, wherein the hydrogel further comprises thiolated gelatin.

8. The method of claim 6, wherein the hydrogel further comprises thiolated collagen.

9. The method of claim 6, wherein the neural stem cell recruiting factor is selected from the group consisting of hepatocyte growth factor, gliotropic factors, human recombinant annexin A2, stem cell factor-1, stromal cell-derived factor-1 (SDF-1), chemokine monocyte chemoattractant protein-1 (MCP-1, SCYA2, CCL2, MCAF), vascular endothelial growth factor (VEGF), epidermal growth factor (EGF), transmembrane protein 18, glioma-produced ECM (tenascin-C), IGF-1, FGF-2, PDGF and any combination thereof.

10. The method of claim 6, wherein the hydrogel further comprises heparin.

---

---

What is claimed is:

1. A method of promoting revascularization in a central nervous system (CNS) lesion, comprising delivering to the lesion an amount of a hydrogel effective to promote revascularization of the lesion, wherein the hydrogel comprises thiolated hyaluronic acid, thiolated polyethylene glycol and a thiolated laminin peptide sequence comprising the amino acid sequence CDPVCCGTARPGYIGSRGTARCCAC (SEQ ID NO:1).

2. The method of claim 1, wherein the hydrogel further comprises thiolated gelatin.

3. The method of claim 1, wherein the hydrogel further comprises thiolated collagen.

4. The method of claim 1, wherein the hydrogel further comprises heparin.

5. A method of promoting revascularization and reenervation of a CNS lesion, comprising delivering to the lesion an amount of a hydrogel effective to promote revascularization and reenervation of the lesion, wherein the hydrogel com- 11. A method of recruiting neural stem cells to a CNS lesion, comprising delivering to the lesion an amount of a hydrogel comprising a neural stem cell recruiting factor, wherein said amount is effective to promote revascularization of the lesion and recruitment of neural stem cells to the lesion, wherein the hydrogel comprises thiolated hyaluronic acid, thiolated polyethylene glycol and a thiolated laminin peptide sequence comprising the amino acid sequence CDPVCCGTARPGYIGSRGTARCCAC (SEQ ID NO:1).

12. The method of claim 11, wherein the neural stem cell recruiting factor is selected from the group consisting of hepatocyte growth factor, gliotropic factors, human recombinant annexin A2, stem cell factor-1, stromal cell-derived factor-1 (SDF-1), chemokine monocyte chemoattractant protein-1 (MCP-1, SCYA2, CCL2, MCAF), vascular endothelial growth factor (VEGF), epidermal growth factor (EGF), transmembrane protein 18, glioma-produced ECM (tenascin-C), IGF-1, FGF-2, PDGF and any combination thereof.

13. A method of repairing a CNS lesion, comprising delivering to the lesion an amount of a hydrogel effective to promote revascularization and reenervation of the lesion, wherein the hydrogel comprises thiolated hyaluronic acid, thiolated polyethylene glycol and a thiolated laminin peptide sequence comprising the amino acid sequence CDPVCCGTARPGYIGSRGTARCCAC (SEQ ID NO:1).

14. A method of preventing scar tissue growth in a CNS lesion, comprising delivering to the lesion an amount of a hydrogel comprising at least one agent that blocks the biosynthesis of inhibitory ECM components, wherein said amount is effective to prevent scarring, wherein the hydrogel comprises thiolated hyaluronic acid, thiolated polyethylene glycol and a thiolated laminin peptide sequence comprising the amino acid sequence CDPVCCGTARPGYIGSRGTARCCAC (SEQ ID NO:1) and wherein the agent is selected from the group consisting of p-nitrophenyl-b-D-xylopyranoside, dimethyloxalylglycine, cyclic nucleotides and any combination thereof.

15. A method of digesting scar tissue in a CNS lesion, comprising delivering to the lesion an amount of a hydrogel comprising at least one ECM-degrading enzyme, wherein said amount is effective to digest scar tissue, wherein the hydrogel comprises thiolated hyaluronic acid, thiolated polyethylene glycol and a thiolated laminin peptide sequence comprising the amino acid sequence CDPVCCGTARPGYIGSRGTARCCAC (SEQ ID NO:1) and wherein the enzyme is selected from the group consisting of chondroitinase ABC, collagenase IV and any combination thereof.

16. A method of maintaining a scar-reduced environment in a CNS lesion, comprising delivering to the lesion an amount of a hydrogel comprising at least one agent that blocks the biosynthesis of inhibitory ECM components and, optionally, at least one ECM-degrading enzyme, wherein said amount is effective to maintain a scar reduced environment, wherein the hydrogel comprises thiolated hyaluronic acid, thiolated polyethylene glycol and a thiolated laminin peptide sequence comprising the amino acid sequence CDPVCCGTARPGYIGSRGTARCCAC (SEQ ID NO:1) and wherein the agent is selected from the group consisting of p-nitrophenyl-b-D-xylopyranoside, dimethyloxalylglycine, cyclic nucleotides and any combination thereof and wherein the enzyme is selected from the group consisting of chondroitinase ABC, collagenase IV and any combination thereof.

* * * * *

UNITED STATES PATENT AND TRADEMARK OFFICE
CERTIFICATE OF CORRECTION

PATENT NO.       : 8,481,067 B2
APPLICATION NO.  : 12/794556
DATED            : July 9, 2013
INVENTOR(S)      : Zhang et al.

It is certified that error appears in the above-identified patent and that said Letters Patent is hereby corrected as shown below:

In the Specification:
Column 1, Line 4: Please insert the following paragraph before the paragraph entitled "PRIORITY STATEMENT"

-- STATEMENT OF GOVERNMENT SUPPORT
This invention was made with government support under Grant No. RR021949 awarded by the National Institutes of Health and Grant Nos. W81XWH-10-1-0954 and W81XWH-08-1-0187 awarded by the Department of Defense. The U.S. Government has certain rights in this invention. --

Column 1, line 16: Please correct "9662-4 ST25.txt,"
to read -- 9662-4_ST25.txt, --

Column 12, line 35: Please correct "*J. Neurosci.* 19:8182 (0.1999);"
to read -- *J. Neurosci.* 19:8182(1999); --

Signed and Sealed this
Twenty-seventh Day of May, 2014

Michelle K. Lee
*Deputy Director of the United States Patent and Trademark Office*